United States Patent

Lebl et al.

(10) Patent No.: US 9,347,440 B2
(45) Date of Patent: *May 24, 2016

(54) FLOW CELLS AND MANIFOLDS HAVING AN ELECTROOSMOTIC PUMP

(75) Inventors: Michal Lebl, San Diego, CA (US); Dale Buermann, Los Altos, CA (US); Mark T. Reed, Menlo Park, CA (US); David L. Heiner, San Diego, CA (US); Alexander Triener, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 760 days.

This patent is subject to a terminal disclaimer.

(21) Appl. No.: 13/442,013

(22) Filed: Apr. 9, 2012

(65) Prior Publication Data

US 2012/0195794 A1    Aug. 2, 2012

Related U.S. Application Data

(63) Continuation of application No. 12/031,054, filed on Feb. 14, 2008, now Pat. No. 8,173,080.

(51) Int. Cl.
*G01N 33/48* (2006.01)
*B01L 3/00* (2006.01)
*F04B 19/00* (2006.01)
(Continued)

(52) U.S. Cl.
CPC ......... *F04B 19/006* (2013.01); *B01L 3/50273* (2013.01); *G01N 35/00613* (2013.01); *B01L 3/502715* (2013.01); *B01L 7/00* (2013.01); *B01L 2300/0816* (2013.01);
(Continued)

(58) Field of Classification Search
CPC .................................................. G01N 35/1095
See application file for complete search history.

(56) References Cited

U.S. PATENT DOCUMENTS 3,923,426 A   12/1975  Theeuwes
5,223,114 A    6/1993  Zane et al.
(Continued)

FOREIGN PATENT DOCUMENTS

WO    WO2006017404 A2    2/2006
WO    WO2007123744 A2    11/2007
WO    WO2008002502 A2    1/2008

OTHER PUBLICATIONS

Examination Report dated Nov. 19, 2013 for European Patent Application No. 09 710 668.6-1558.
(Continued)

*Primary Examiner* — Jill Warden
(74) *Attorney, Agent, or Firm* — Dean D. Small; Jason P. Gross; The Small Patent Law Group, LLC

(57) ABSTRACT

A flow cell for use in a microfluidic detection system. The flow cell includes a flow cell body having a channel that extends along the flow cell body. The flow cell body has a substrate material that extends along the channel and that is transparent to at least one of excitation light or light emissions. The channel has a functionalized channel surface that includes reactive groups configured to attach to molecules for biochemical analysis. The flow cell also includes fluidic inlet and fluidic outlet ports provided on the flow cell body and an electroosmotic (EO) pump held within the flow cell body in fluid communication with the channel. The EO pump is operable to induce flow of a solution from the inlet port to the outlet port and along the functionalized channel surface.

30 Claims, 15 Drawing Sheets

(51) Int. Cl.
*G01N 35/00* (2006.01)
*G01N 35/10* (2006.01)
*B01L 7/00* (2006.01)

(52) U.S. Cl.
CPC . *B01L 2300/0877* (2013.01); *B01L 2400/0418* (2013.01); *G01N 35/1095* (2013.01); *Y10T 436/2575* (2015.01)

(56) References Cited

U.S. PATENT DOCUMENTS

| | | | |
|---|---|---|---|
| 5,580,435 | A | 12/1996 | Kovacs |
| 6,391,622 | B1 | 5/2002 | Knapp et al. |
| 6,488,831 | B1 | 12/2002 | Hayes |
| 6,857,449 | B1 | 2/2005 | Chow |
| 6,890,411 | B1 | 5/2005 | Hayes et al. |
| 6,942,018 | B2 | 9/2005 | Goodson et al. |
| 6,991,024 | B2 | 1/2006 | Goodson et al. |
| 7,001,608 | B2 | 2/2006 | Fishman et al. |
| 7,037,416 | B2 | 5/2006 | Parce et al. |
| 7,070,681 | B2 | 7/2006 | Santiago et al. |
| 7,131,486 | B2 | 11/2006 | Goodson et al. |
| 7,134,486 | B2 | 11/2006 | Santiago et al. |
| 7,147,865 | B2 | 12/2006 | Fishman et al. |
| 7,185,697 | B2 | 3/2007 | Goodson et al. |
| 7,201,833 | B2 | 4/2007 | Lauks et al. |
| 7,231,839 | B2 | 6/2007 | Huber et al. |
| 7,238,323 | B2 | 7/2007 | Knapp et al. |
| 7,316,543 | B2 | 1/2008 | Goodson et al. |
| 2003/0127329 | A1* | 7/2003 | DeVoe et al. ............ 204/454 |
| 2003/0226604 | A1 | 12/2003 | Schlautmann et al. |
| 2004/0115838 | A1 | 6/2004 | Quake et al. |
| 2004/0120827 | A1 | 6/2004 | Kim et al. |
| 2004/0163957 | A1 | 8/2004 | Neyer et al. |
| 2005/0009101 | A1* | 1/2005 | Blackburn ............... 435/7.1 |
| 2005/0061669 | A1 | 3/2005 | Woudenberg et al. |
| 2005/0205241 | A1* | 9/2005 | Goodson et al. ......... 165/80.4 |
| 2006/0029851 | A1 | 2/2006 | Santiago et al. |
| 2006/0215155 | A1 | 9/2006 | Weber |
| 2006/0254913 | A1 | 11/2006 | Myers et al. |
| 2007/0009366 | A1 | 1/2007 | Myers et al. |
| 2007/0037225 | A1 | 2/2007 | Metzger et al. |
| 2007/0102293 | A1 | 5/2007 | Tai et al. |
| 2007/0202525 | A1 | 8/2007 | Quake et al. |

OTHER PUBLICATIONS

Devasenathipathy, Shankar et al; "Particle Tracking Techniques for Electrokinetic Microchannel Flows"; Anal. Chem. 2002, 74, 3704-3713.
Kim, Daejoong et al; "High Flow Rate Per Power Pumping of Aqueous Solutions and Organic solvents with Electroosmotic Pumps", IMECE2005-81198; Nov. 5-11, 2005, 4 pgs.
Seiler, K. et al; "Electroosmotic Pumping and Valveless Control of Fluid-Flow Within a Manifold of Capillaries on a Glass Chip"; Abstract; 1pg.
Tripp, Jennifer A. et al; :High Pressure Electroosmotic Pumps Based on Porous Polymer Mooliths, Sensors and Actuators B 99 (2004) 66-73.
Wu, Junqing et al; "AC Electrokinetic Pumps for Micro/NanoFLuidics"; IMECE2004-61836; Nov. 2004; 10pgs.
Yao, Shuhuai et al; "Porous Glass Electroosmotic Pumps: Theory"; Journal of colloid and Interface Scienc 268 (2003) 133-142.
Yao, Shuhauai et al; "Electroosmotic Pumps Fabricated from Porous Silicon Membranes"; Journal of Microelectromechanical Systems, vol. 15, No. 3, Jun. 2006, 717-728.
Gast, F. et al; "The Microscopy cell (MicCell), a versatile modular flowthrough system for cell biology, biomaterial research, and nanotechnology"; Microfluid Nanofluid (2006) 2: 21-36.
Chen, Z et al; An Electro-osmotic micro-pump based on monolithic silica for micro-flow analyses and electro-sprays, Anal Bioanal Chem (2005) 382: 817-824.
Brask, Anders; "Electroosmotic Micropumps"; PhD Thesis, s961052; Aug. 31, 2005; 151pgs.
International Written Opinion and Search Report for PCT/US2009/033637, mailed on Jul. 16, 2010.

\* cited by examiner

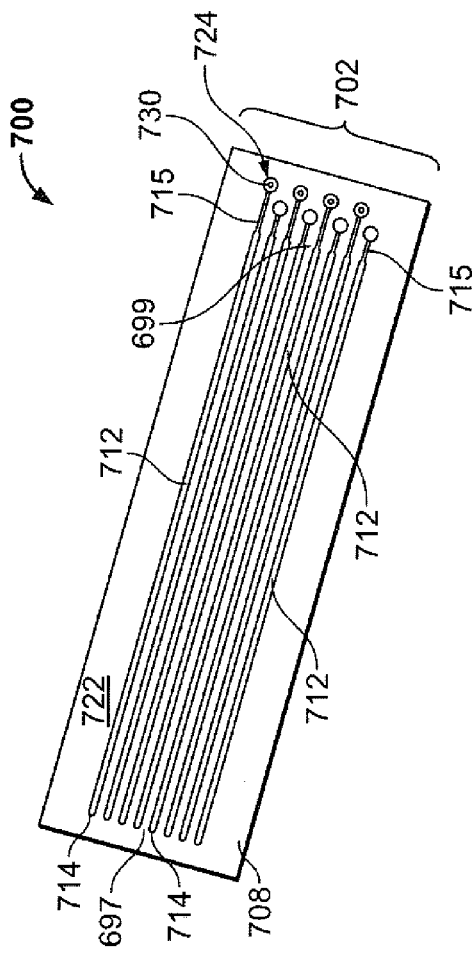
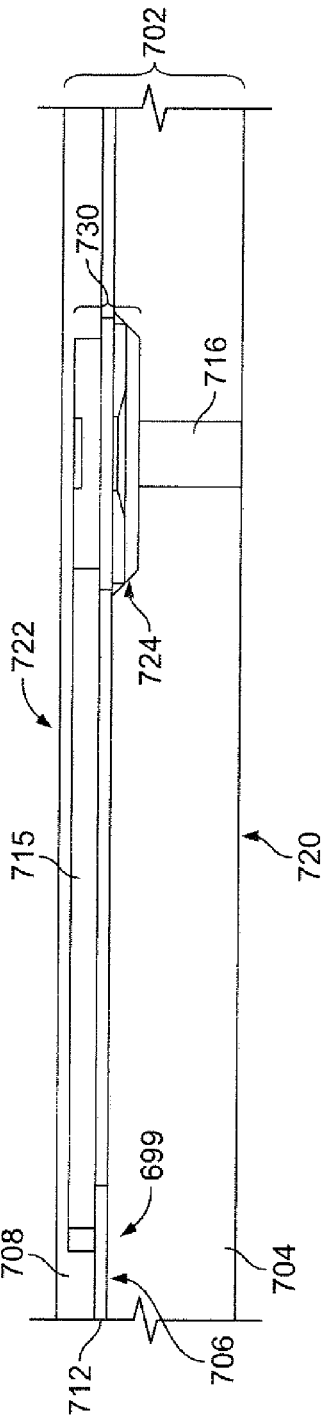
FIG. 6
FIG. 7

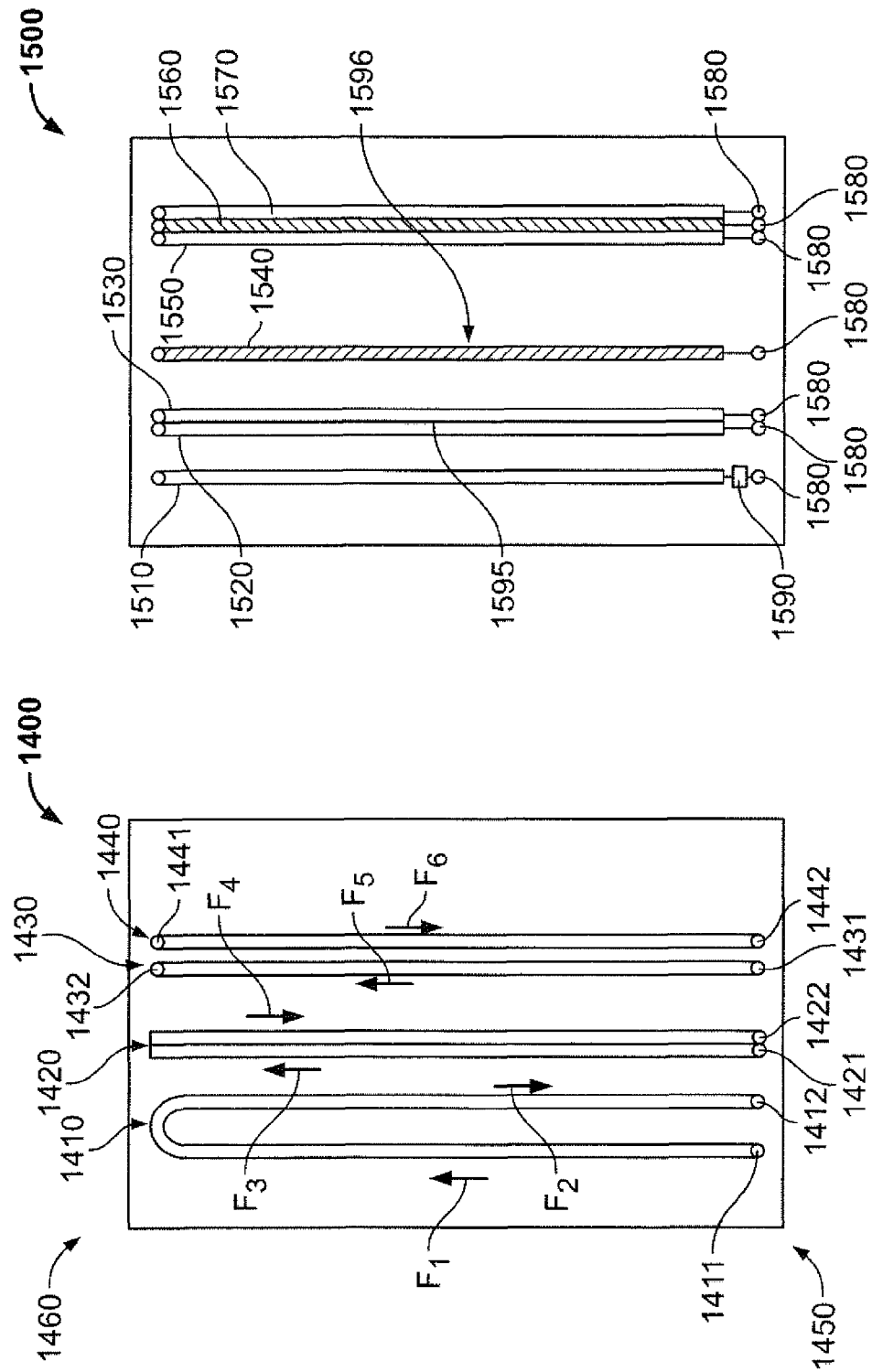

FLOW CELLS AND MANIFOLDS HAVING AN ELECTROOSMOTIC PUMP

CROSS-REFERENCE TO RELATED APPLICATIONS

The present application is a continuation of U.S. application Ser. No. 12/031,054, filed on Feb. 14, 2008 and entitled "Flow Cells and Manifolds Having an Electroosmotic Pump," which is incorporated by reference in its entirety.

BACKGROUND OF THE INVENTION

The invention relates generally to microfluidic systems, and more particularly to microfluidic flow cells and manifolds that may be used in biochemical analysis.

Numerous recent advances in the study of biology have benefited from improved methods of analysis and sequencing of nucleic acids. For example, the Human Genome Project has determined the sequence of the human genome. However, there are still vast amounts of genomic material to analyze, e.g., genetic variation between different individuals, tissues, the genomes of additional species, etc.

In order to expedite the analysis of genetic material, a number of new DNA sequencing technologies have recently been reported that are based on the parallel analysis of amplified and unamplified molecules. These new technologies frequently rely upon the detection of fluorescent nucleotides and oligonucleotides. Furthermore, these new technologies frequently depend upon heavily automated processes that must perform at a high level of precision. For example, a computing system may control a fluid flow subsystem that is responsible for initiating several cycles of reactions within a microfluidic flow cell. These cycles may be performed with different solutions and/or temperature and flow rates. However, in order to control the fluid flow subsystem a variety of pumping devices must be operated. Some of these devices have movable parts that may disturb or negatively affect the reading and analyzing of the fluorescent signals. Furthermore, after each cycle the pumps may need to be exchanged or cleaned thereby increasing the amount of time to complete the cycles.

Thus, there is a need in the industry for flow cells or other microfluidic components that do not have movable parts and/or facilitate reducing the amount of time necessary to complete analyses.

BRIEF DESCRIPTION OF THE INVENTION

In one embodiment, a flow cell for use in a microfluidic detection system is provided. The flow cell includes a flow cell body having a channel that is configured to convey a solution through the flow cell body. The flow cell also includes a bottom surface and a top surface. The bottom surface is configured to be removably held by the detection system, and the top surface is transparent and permits light to pass therethrough. The flow cell body also includes fluidic inlet and outlet ports that are in fluid communication with the channel. A pump cavity is also provided in the flow cell body. The pump cavity fluidly communicates with, and is interposed between, an end of the channel and one of the fluidic inlet and outlet ports. An electroosmotic (EO) pump is held in the pump cavity. The EO pump induces flow of the solution through the EO pump and channel between the fluidic inlet and outlet ports.

Optionally, the flow cell may include contacts that are disposed on at least one of the top and bottom surfaces of the flow cell body. The contacts are electrically coupled to the EO pump. In addition, the EO pump includes a porous membrane core that is positioned between electrodes that induce a flow rate of the liquid through the porous core membrane based on a voltage potential maintained between the electrodes.

In one embodiment, a manifold for attaching to a detector subsystem within a microfluidic analysis system is provided. The manifold includes a housing that has a detector engaging end and a line terminating end. The housing has an internal passageway that extends therethrough and is configured to convey a solution. The detector engaging end is configured to be removably coupled to the detector subsystem. The passageway has one end that terminates at a passage inlet provided at the detector engaging end of the housing. The passage inlet is configured to sealably mate with a fluidic outlet port on the detector system. The line terminating end includes at least one receptacle that is configured to be coupled to a discharge line. The passageway has another end that terminates at a passage outlet at the receptacle. The passage outlet is configured to sealably mate with a connector on the discharge line. A pump cavity is also provided in the housing. The pump cavity is in fluid communication with, and interposed between, an end of the passageway and one of the passage inlet and outlet. The manifold also includes an electroosmotic (EO) pump that is held in the pump cavity. The EO pump induces flow of the solution through the EO pump and passageway between the passageway inlet and outlet.

Optionally, the EO pump may include a tubular-shaped porous membrane core having disc-shaped anode and cathode electrodes that are arranged concentrically about the core. The EO pump may also include a vapor permeable collar and a catalyst collar that are arranged about the core and held between the anode and cathode electrodes.

BRIEF DESCRIPTION OF THE DRAWINGS

FIG. 6 is a planar view of a flow cell that integrates an electroosmotic (EO) pump formed in accordance with one embodiment.

FIG. 7 is a cross-sectional view of the flow cell shown in FIG. 6.

FIG. 17 is a planar view of a flow cell formed in accordance with an alternative embodiment FIG. 18 is a planar view of a flow cell that integrates one or more heating mechanisms.

DETAILED DESCRIPTION OF THE INVENTION

Figure 1:
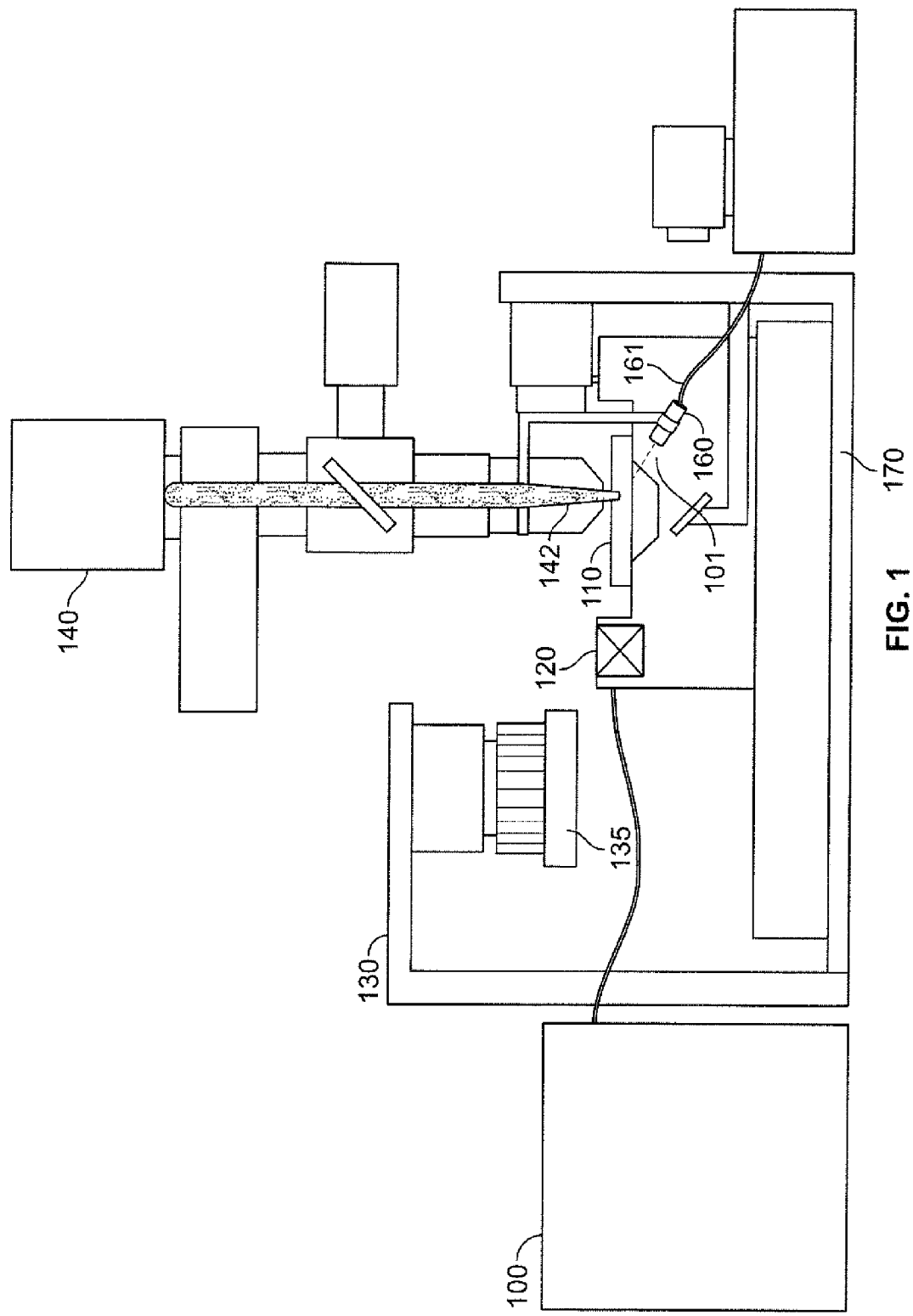
FIG. 1 illustrates a system that may be formed in accordance with one embodiment.

Embodiments described herein include systems, flow cells, and manifolds (or other microfluidic devices) that may be used for the creation and/or analysis of analyte arrays, such as nucleic acid arrays. In particular, embodiments of the arrays are formed by creating nucleic acid clusters through nucleic acid amplification on solid surfaces. Some embodiments may include several subsystems that interact with each other to create, read, and analyze the arrays. The subsystems may include a fluid flow subsystem, temperature control subsystem, light and reader subsystem, a moving stage which may hold the flow cells and manifolds, and a computing subsystem that may operate the other subsystems and perform analysis of the readings. In particular, some of the systems and devices may be integrated with or include electroosmotic (EO) pumps. Some of the EO pumps that may be used with the systems and devices discussed herein are described in U.S. patent application Ser. No. 11/168,779 (Publication No. 2007/0009366); Ser. No. 11/125,720 (Publication No. 2006/0254913); and Ser. No. 10/912,527 (Publication No. 2006/0029851); all of which are incorporated by reference in their entirety. Furthermore, the systems and devices include various combinations of optical, mechanical, fluidic, thermal, electrical, and computing aspects/features. Although portions of these are described herein, these aspects/features may be more fully described in international patent application no. PCT/US2007/007991 (published as WO 2007/123744), which claims priority to U.S. provisional application Nos. 60/788,248 and 60/795,368, and in international patent application no. PCT/US2007/014649 (published as WO 2008/002502), which claims priority to U.S. provisional application No. 60/816,283, all of which are incorporated by reference in their entirety.

The terminology used herein is for the purpose of describing particular embodiments only, and is not intended to be limiting. For example, "a flow cell," as used herein, may have one or more fluidic channels in which a chemical analyte, such as a biochemical substance, is displayed (e.g., wherein the chemical analytes are polynucleotides that are directly attached to the flow cell or wherein the chemical analytes are polynucleotides that are attached to one or more beads or other substrates arrayed upon the flow cell) and may be fabricated from glass, silicon, plastic, or combinations thereof. Other analytes that can be detected using the apparatus or methods described herein include libraries of proteins, peptides, saccharides, biologically active molecules, synthetic molecules or the like. For purposes of explanation the apparatus and methods are exemplified below in the context of nucleic acid sequencing. However, it should be understood that other applications include use of these other analytes, for example, to evaluate RNA expression, genotyping, proteomics, small molecule library synthesis, or the like.

Furthermore, a flow cell may include a combination of two or more flow cells, and the like. As used herein, the terms "polynucleotide" or "nucleic acids" refer to deoxyribonucleic acid (DNA), ribonucleic acid (RNA), or analogs of either DNA or RNA made from nucleotide analogs. The terms as used herein also encompasses cDNA, that is complementary, or copy, DNA produced from an RNA template, for example by the action of reverse transcriptase. In some embodiments, the nucleic acid to be analyzed, for example by sequencing, through use of the described systems is immobilized upon a substrate (e.g., a substrate within a flow cell or one or more beads upon a substrate such as a flow cell, etc.). The term "immobilized" as used herein is intended to encompass direct or indirect, covalent or non-covalent attachment, unless indicated otherwise, either explicitly or by context. The analytes (e.g. nucleic acids) may remain immobilized or attached to the support under conditions in which it is intended to use the support, such as in applications requiring nucleic acid sequencing.

The term "solid support" (or "substrate"), as used herein, refers to any inert substrate or matrix to which nucleic acids can be attached, such as for example glass surfaces, plastic surfaces, latex, dextran, polystyrene surfaces, polypropylene surfaces, polyacrylamide gels, gold surfaces, and silicon wafers. For example, the solid support may be a glass surface (e.g., a planar surface of a flow cell channel). In some embodiments, the solid support may comprise an inert substrate or matrix which has been "functionalized," such as by applying a layer- or coating of an intermediate material comprising reactive groups which permit covalent attachment to molecules such as polynucleotides. By way of non-limiting example, such supports can include polyacrylamide hydrogels supported on an inert substrate such as glass. The molecules (polynucleotides) can be directly covalently attached to the intermediate material (e.g. the hydrogel) but the intermediate material can itself be non-covalently attached to the substrate or matrix (e.g. the glass substrate). The support can include a plurality of particles or beads each having a different attached analyte.

In some embodiments, the systems described herein may be used for sequencing-by-synthesis (SBS). In SBS, four fluorescently labeled modified nucleotides are used to sequence dense clusters of amplified DNA (possibly millions of clusters) present on the surface of a substrate (e.g., a flow cell). The flow cells containing the nucleic acid samples for sequencing can take the form of arrays of discrete, separately detectable single molecules, arrays of features (or clusters) containing homogeneous populations of particular molecular species, such as amplified nucleic acids having a common sequence, or arrays where the features are beads comprising molecules of nucleic acid. The nucleic acids can be prepared such that the nucleic acids include an oligonucleotide primer adjacent to an unknown target sequence. To initiate the first SBS sequencing cycle, one or more differently labeled nucleotides, and DNA polymerase, etc., can be flowed into/through the flow cell by a fluid flow subsystem. Either a single nucleotide can be added at a time, or the nucleotides used in the sequencing procedure can be specially designed to possess a reversible termination property, thus allowing each cycle of the sequencing reaction to occur simultaneously in the presence of all four labeled nucleotides (A, C, T, G). Where the four nucleotides are mixed together, the polymerase is able to select the correct base to incorporate and each sequence is extended by a single base. In such methods of using the systems, the natural competition between all four alternatives leads to higher accuracy than wherein only one nucleotide is present in the reaction mixture (where most of the sequences are therefore not exposed to the correct nucleotide). Sequences where a particular base is repeated one after another (e.g., homopolymers) are addressed like any other sequence and with high accuracy.

FIG. 1 illustrates a detector system 50 that may be formed in accordance with one embodiment. The system 50 may include a fluid flow subsystem 100 for directing the flow of reagents (e.g., fluorescent nucleotides, buffers, enzymes, cleavage reagents, etc.) or other solutions to and through a flow cell 110 and waste valve 120. As will be discussed in greater detail below, the fluid flow system 100 and the flow cell 110 may include EO pumps. The flow cell 110 may have clusters of nucleic acid sequences (e.g., of about 200-1000 bases in length) to be sequenced which are optionally attached to the substrate of the flow cell 110, as well as optionally other components. The flow cell 110 may also include an array of beads, where each bead optionally contains multiple copies of a single sequence. The system 50 may also include a temperature control subsystem 135 to regulate the reaction conditions within the flow cell channels and reagent storage areas/containers (and optionally the camera, optics, and/or other components). In some embodiments, a heating/cooling element, which may be part of the temperature control subsystem 135, is positioned underneath the flow cell 110 in order to heat/cool the flow cell 110 during operation of the system 50. An optional movable stage 170 upon which the flow cell 110 is placed allows the flow cell to be brought into proper orientation for laser (or other light 101) excitation of the substrate and optionally moved in relation to a lens 142 and camera system 140 to allow reading of different areas of the substrate. Additionally, other components of the system are also optionally movable/adjustable (e.g., the camera, the lens objective, the heater/cooler, etc.).

The flow cell 110 is monitored, and sequencing is tracked, by camera system 140 (e.g., a CCD camera) which can interact with various filters within a filter switching assembly (not shown), lens 142, and focusing laser/focusing laser assembly (not shown). A laser device 160 (e.g., an excitation laser within an assembly optionally comprising multiple lasers) may illuminate fluorescent sequencing reactions within the flow cell 110 via laser illumination through fiber optic 161 (which can optionally include one or more re-imaging lenses, a fiber optic mounting, etc.). It will be appreciated that the illustrations herein are of exemplary embodiments and are not necessarily to be taken as limiting.

Figure 2:
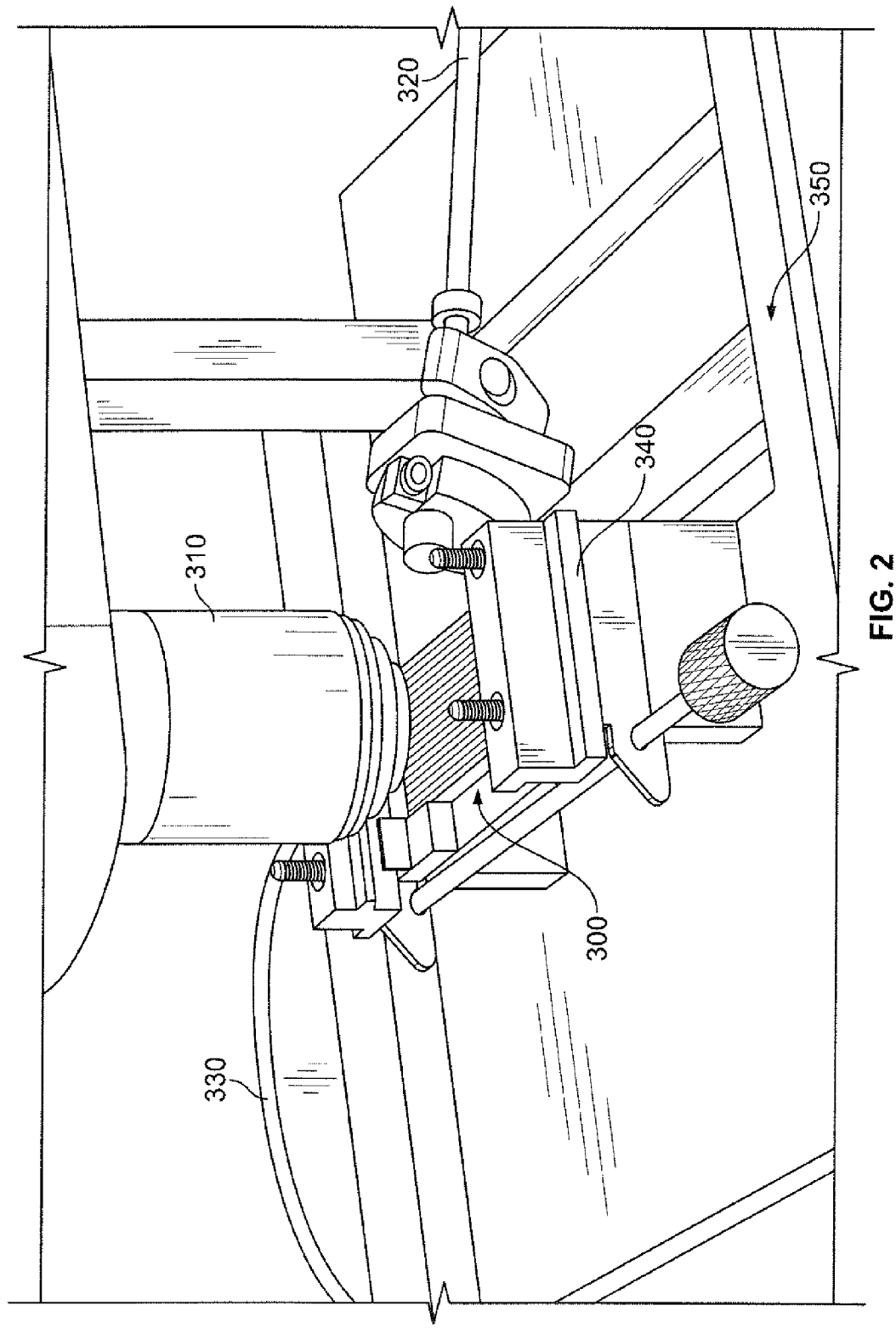
FIG. 2 is a perspective of a reader subsystem that may be used with the system shown in FIG. 1.

FIG. 2 illustrates a reader subsystem with a flow cell 300 that may be used with an imaging or sequencing system, such as the detector system 50 described above in FIG. 1. As shown, when nucleic acid samples have been deposited on the surface of the flow cell 300, a laser coupled through optical fiber 320 may be positioned to illuminate the flow cell 300. An objective lens component 310 may be positioned above the flow cell 300 and capture and monitor the various fluorescent emissions once the fluorophores are illuminated by a laser or other light. Also shown, the reagents may be directed through the flow cell 300 through one or more tubes 330 which connect to the appropriate reagent storage, etc. The flow cell 300 may be placed within a flow cell holder 340, which may be placed upon movable staging area 350. The flow cell holder 340 may hold the flow cell 300 securely in the proper position or orientation in relation to the laser, the prism (not shown), which directs laser illumination onto the imaging surface, and the camera system, while the sequencing occurs. Alternatively, the objective lens component 310 is positioned below the flow cell 300. The laser may be similarly positioned as shown in FIG. 2 or may be adjusted accordingly for the objective lens component 310 to read the fluorescent emissions. In another alternative embodiment, the flow cell 300 may be viewable from both sides (i.e., top and bottom). As such, the multiple readers or imaging systems may be used to read signals emanating from the channels of the flow cells 300.

Figure 3A:
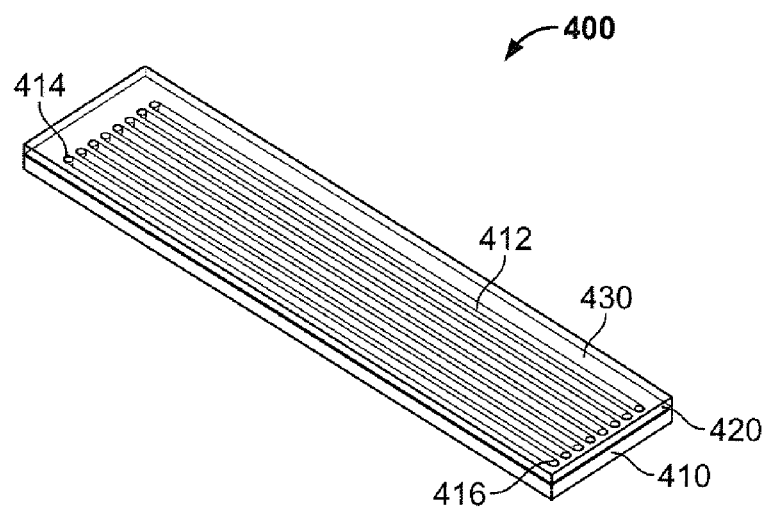
FIG. 3A illustrates a flow cell formed in accordance with one embodiment.
Figure 3B:
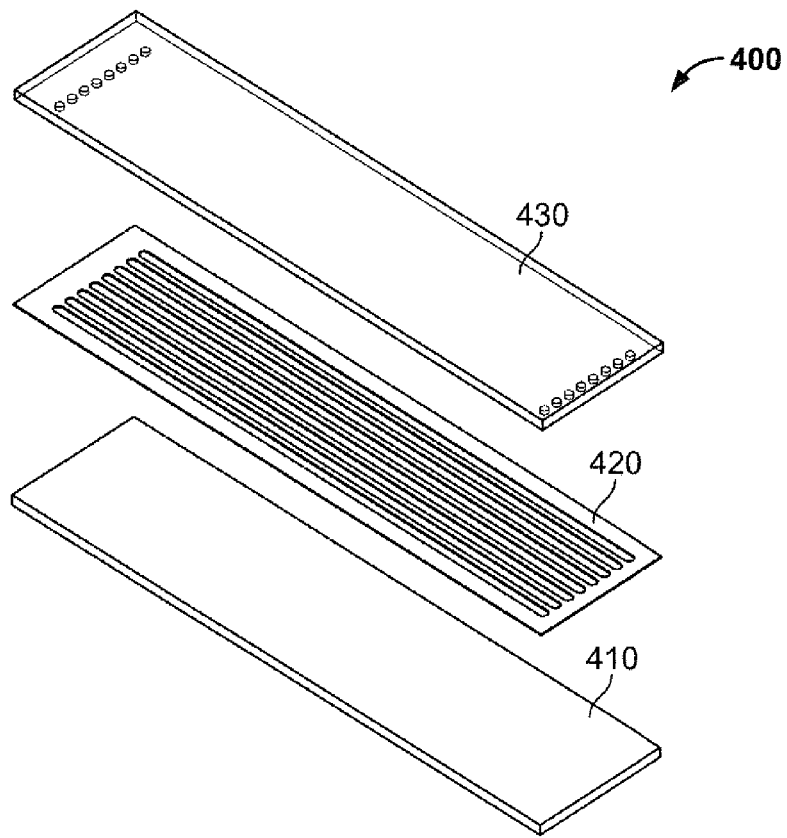
FIG. 3B illustrates an exploded view of the flow cell of FIG. 3A.

FIGS. 3A and 3B display a flow cell 400 formed in accordance with one embodiment. The flow cell 400 includes a bottom or base layer 410 (e.g., of borosilicate glass 1000 μm in depth), a channel spacer or layer 420 (e.g., of etched silicon 100 μm in depth) overlaying the base layer 410, and a cover layer 430 (e.g., 300 μm in depth). When assembled, the layers 410, 420, and 430 form enclosed channels 412 having inlets and outlets ports 414 and 416, respectively, at either end through the cover layer 430. As will be discussed in greater detail below, the flow cell 400 may be configured to engage or sealably mate with a manifold, such as manifold 810. Alternatively, the inlets 414 and outlets 416 of the flow cell 400 may open at the bottom of or on the sides of the flow cell 400. Furthermore, while the flow cell 400 includes eight (8) channels 412, alternative embodiments may include other numbers. For example, the flow cell 400 may include only one (1) channel 412 or possibly two (2), three (3), four (4), sixteen (16) or more channels 412. In one embodiment, the channel layer 420 may be constructed using standard photolithographic methods. One such method includes exposing a 100 μm layer of silicon and etching away the exposed channel using Deep Reactive Ion Etching or wet etching.

Figure 3C:
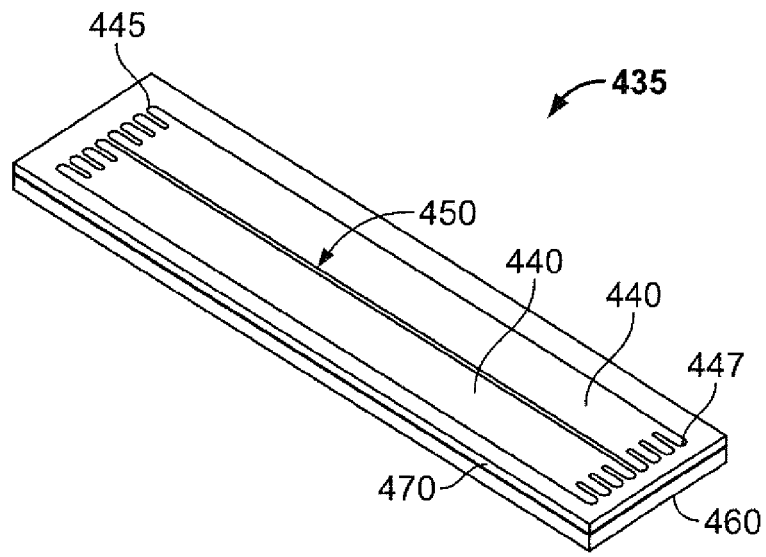
FIG. 3C illustrates a flow cell in accordance with an embodiment having channels that are wider than the channels of the flow cell of FIG. 3A.
Figure 3D:
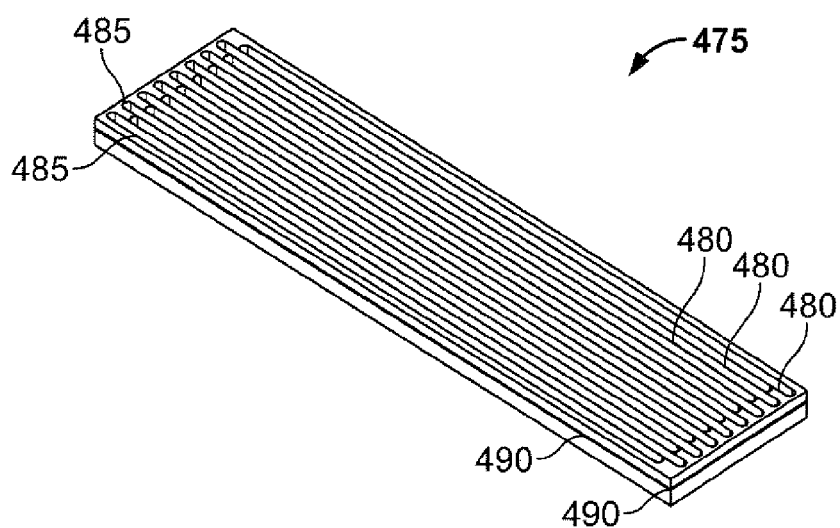
FIG. 3D illustrates a flow cell having offset channels in accordance with an embodiment.

Additionally, the channels 412 may have different depths and/or widths (different both between channels in different flow cells and different between channels within the same flow cell). For example, while the channels 412 formed in the cell in FIG. 3B are 100 μM deep, other embodiments can optionally comprise channels of greater depth (e.g., 500 μm) or lesser depth (e.g., 50 μm). FIGS. 3C and 3D illustrate flow cell configurations formed in accordance with alternative embodiments. As shown in FIG. 3C, flow cells 435 may have channels 440, which are wider than the channels 412 described with reference to the flow cell 400, or two channels having a total of eight (8) inlet and outlet ports 445 and 447. The flow cell 435 may include a center wall 450 for added structural support. In the example of FIG. 3D, the flow cell 475 may include offset channels 480 such that the inlet and outlet ports 485 and 490, respectively, are arranged in staggered rows at opposite ends of the flow cell 475.

The flow cells may be formed or constructed from a number of possible materials. For example, the flow cells may be manufactured from photosensitive glass(es) such as Foturan® (Mikroglas, Mainz, Germany) or Fotoform® (Hoya, Tokyo, Japan), which may be formed and manipulated as necessary. Other possible materials can include plastics such as cyclic olefin copolymers (e.g., Topas® (Ticona, Florence, Ky.) or Zeonor® (Zeon Chemicals, Louisville, Ky.)) which have excellent optical properties and can withstand elevated temperatures. Furthermore, the flow cells may be made from a number of different materials within the same flow cell. Thus, in some embodiments, the base layer, the walls of the channels, and the cover layer can optionally be of different materials. Also, while the example in FIG. 3B shows a flow cell 400 formed of three (3) layers, other embodiments can include two (2) layers, e.g., a base layer having channels etched/ablated/formed within it and a cover layer, etc. Other embodiments can include flow cells having only one layer which comprises the flow channel etched/ablated/otherwise formed within it.

Figure 4:
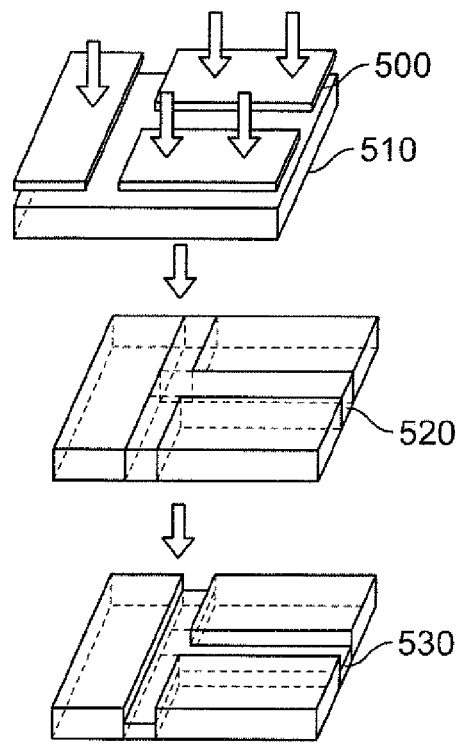
FIG. 4 is a schematic diagram of a process for patterning a flow cell in accordance with one embodiment.

FIG. 4 gives a schematic diagram of a process for patterning a flow cell in accordance with one embodiment. First, the desired pattern is masked out with masks 500, onto the surface of substrate 510 which is then exposed to UV light. The glass is exposed to UV light at a wavelength between 290 and 330 nm. During the UV exposure step, silver or other doped atoms are coalesced in the illuminated areas (areas 520). Next, during a heat treatment between 5000° C. and 6000° C., the glass crystallizes around the silver atoms in area 520. Finally, the crystalline regions, when etched with a 10% hydrofluoric acid solution at room temperature (anisotropic etching), have an etching rate up to 20 times higher than that of the vitreous regions, thus resulting in channels 530. If wet chemical etching is supported by ultrasonic etching or by spray-etching, the resulting structures display a large aspect ratio.

Figure 5A:
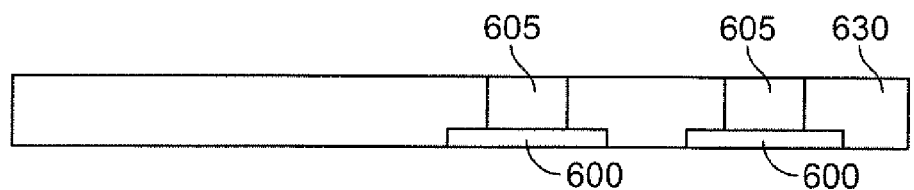
FIG. 5A illustrates an end view of a two-layer flow cell in accordance with an embodiment that includes channels and through-holes.
Figure 5B:
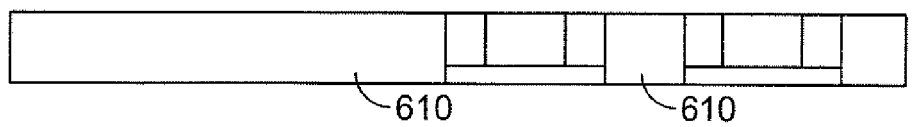
FIG. 5B illustrates the flow cell of FIG. 5A having optically opaque areas.
Figure 5C:
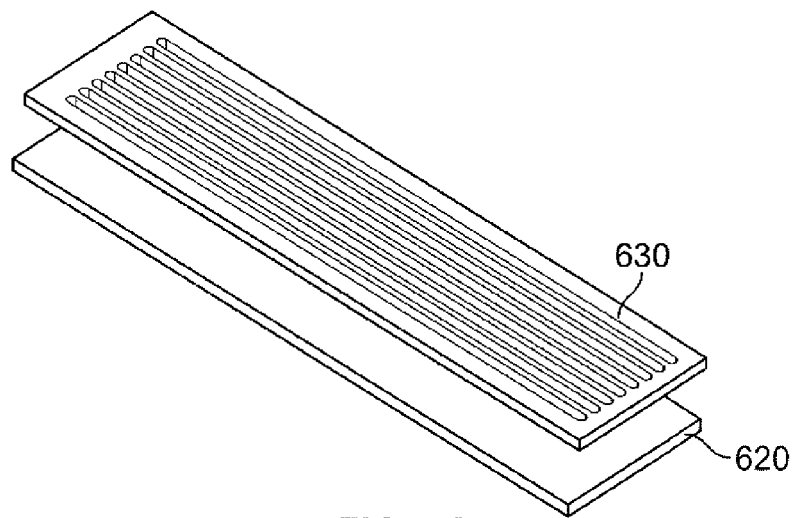
FIG. 5C illustrates a bottom layer and a cover layer of the flow cell of FIG. 5A positioned to be attached to each other.
Figure 5D:
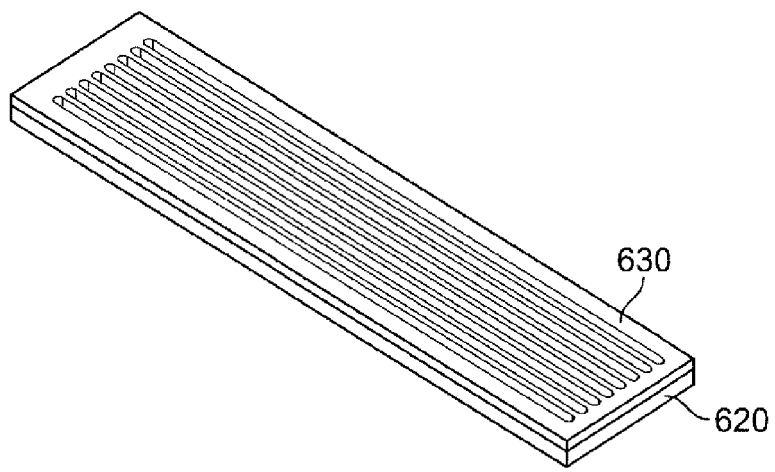
FIG. 5D illustrates the bottom layer and the cover layer of the flow cell of FIG. 5A attached to each other.
Figure 5E:
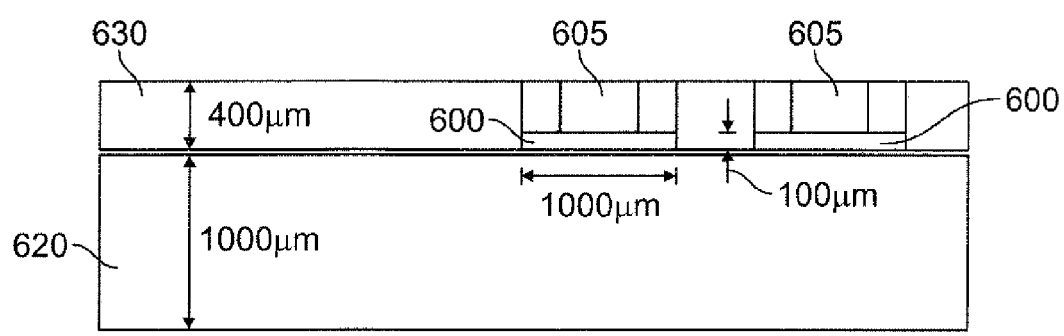
FIG. 5E shows a cutaway view of the flow cell of FIG. 5A after the bottom layer and the cover layer are joined.

FIGS. 5A-E show an etching process that may be used to construct a flow cell in accordance with one embodiment. FIG. 5A illustrates an end view of a two-layer flow cell that includes channels 600 and through-holes 605. The channels 600 and through-holes 605 are exposed/etched into a cover layer 630. The cover layer 630 mates with a bottom layer 620 (shown in FIG. 5E). The through-holes 605 are configured to allow reagents/fluids to enter into the channels 600. The channels 600 can be etched into layer 630 through a 3-D process such as those available from Invenios (Santa Barbara, Calif.). The cover layer 630 may include Foturan and may be UV etched. Foturan, when exposed to UV, changes color and becomes optically opaque (or pseudo-opaque). In FIG. 5B, the cover layer 630 has been masked and light exposed to produce optically opaque areas 610 within the layer. The optically opaque areas may facilitate blocking misdirected light, light scatter, or other nondesirable reflections that could otherwise negatively affect the quality of sequence reading. In alternative embodiments, a thin (e.g., 100-500 nm) layer of metal such as chrome or nickel is optionally deposited between the layers of the flow cell (e.g., between the cover and bottom layers in FIG. 5E) to help block unwanted light scattering. FIGS. 5C and 5D display the mating of bottom layer 620 with cover layer 630 and FIG. 5E shows a cut away view of the same.

The layers of the flow cells may be attached to one another in a number of different ways. For example, the layers can be attached via adhesives, bonding (e.g., heat, chemical, etc.), and/or mechanical methods. Those skilled in the art will be familiar with numerous methods and techniques to attach various glass/plastic/silicon layers to one another. Furthermore, while particular flow cell designs and constructions are described herein, such descriptions should not necessarily be taken as limiting. Other flow cells can include different materials and designs than those presented herein and/or can be created through different etching/ablation techniques or other creation methods than those disclosed herein. Thus, particular flow cell compositions or construction methods should not necessarily be taken as limiting on all embodiments.

The reagents, buffers, and other materials that may be used in sequencing are regulated and dispensed via the fluid flow subsystem 100 (FIG. 1). In general, the fluid flow subsystem 100 transports the appropriate reagents (e.g., enzymes, buffers, dyes, nucleotides, etc.) at the appropriate rate and optionally at the appropriate temperature, from reagent storage areas (e.g., bottles, or other storage containers) through the flow cell 110 and optionally to a waste receiving area. The fluid flow subsystem 100 may be computer controlled and can optionally control the temperature of the various reagent components. For example, certain components are optionally held at cooled temperatures such as 4° C.+/−1° C. (e.g., for enzyme containing solutions), while other reagents are optionally held at elevated temperatures (e.g., buffers to be flowed through the flow cell when a particular enzymatic reaction is occurring at the elevated temperature).

In some embodiments, various solutions are optionally mixed prior to flow through the flow cell 110 (e.g., a concentrated buffer mixed with a diluent, appropriate nucleotides, etc.). Such mixing and regulation is also optionally controlled by the fluid flow subsystem 100. Furthermore, it may be advantageous to minimize the distance between the components of the system 50. There may be a 1:1 relationship between pumps and flow channels, or the flow channels may bifurcate and/or be combined into one channel at various parts of the fluid subsystem. The fluidic reagents may be stored in reagent containers (e.g., buffers at room temperature, 5×SSC buffer, enzymology buffer, water, cleavage buffer, cooled containers for enzymes, enzyme mixes, water, scanning mix, etc.) that are all connected to the fluid flow subsystem 100.

Multi-way valves may also be used to allow controllable access of/to multiple lines/containers. A priming pump may be used to draw reagents from the containers up through the tubing so that the reagents are "ready to go" into the flow cell 110. Thus, dead air, reagents at the wrong temperature (e.g., because of sitting in tubing), etc. may be avoided. The fluid flow itself is optionally driven by any of a number of pump types, (e.g., positive/negative displacement, vacuum, peristaltic, and electroosmotic, etc.).

Which ever pump/pump type is used herein, the reagents are optionally transported from their storage areas to the flow cell 110 through tubing. Such tubing, such as PTFE, can be chosen in order to, e.g., minimize interaction with the reagents. The diameter of the tubing can vary between embodiments (and/or optionally between different reagent storage areas), but can be chosen based on, e.g., the desire to decrease "dead volume" or the amount of fluid left in the lines Furthermore, the size of the tubing can optionally vary from one area of a flow path to another. For example, the tube size from a reagent storage area can be of a different diameter than the size of the tube from the pump to the flow cell, etc.

The fluid flow system 100 can be further equipped with pressure sensors that automatically detect and report features of the fluidic performance of the system, such as leaks, blockages and flow volumes. Such pressure or flow sensors can be useful in instrument maintenance and troubleshooting. The fluidic system can be controlled by the one or more computer component, e.g., as described below. It will be appreciated that the fluid flow configurations in the various embodiments can vary, e.g., in terms of number of reagent containers, tubing length, diameter, and composition, types of selector valves and pumps, etc.

As described above, the various components of the system 50 (FIG. 1) may be coupled to a processor or computing system that functions to instruct the operation of these instruments in accordance with preprogrammed or user input instructions, receive data and information from these instruments, and interpret, manipulate and report this information to the user. As such, the computing system is typically appropriately coupled to these instruments/components (e.g., including an analog to digital or digital to analog converter as needed). The computing system may include appropriate software for receiving user instructions, either in the form of user input into set parameter fields, e.g., in a GUI, or in the form of preprogrammed instructions, e.g., preprogrammed for a variety of different specific operations (e.g., auto focusing, SBS sequencing, etc.). The software may then convert these instructions to appropriate language for instructing the correct operation to carry out the desired operation (e.g., of fluid direction and transport, autofocusing, etc.). Additionally, the data, e.g., light emission profiles from the nucleic acid arrays, or other data, gathered from the system can be outputted in printed form. The data, whether in printed form or electronic form (e.g., as displayed on a monitor), can be in various or multiple formats, e.g., curves, histograms, numeric series, tables, graphs and the like.

FIGS. 6 and 7 illustrate a flow cell 700 that may be formed in accordance with one embodiment. FIG. 6 is a planar view of the flow cell 700, and FIG. 7 is a cross-sectional view of a portion of the flow cell 700. The flow cell 700 may have similar features and may be similarly formed as described above with respect to the flow cells illustrated in FIGS. 2, 3A-3D, 4, and 5A-E. As shown, the flow cell 700 includes a flow cell body 702 that may be formed from one or more substrate layers stacked upon each other. As shown in FIG. 7, the flow cell body 702 includes a bottom layer 704, a channel spacer or layer 706, and a cover layer 708. The channel spacer 706 may be optically opaque in order to block misdirected light, light scatter, or other nondesirable reflections that could otherwise negatively affect the quality of sequence reading. The flow cell body 702 has a substantially planar bottom surface 720 (FIG. 7) and a substantially planar top surface 722. The surfaces 720 and 722 may be transparent allowing light to pass therethrough, and either surface 720 or 722 (and corresponding layers 704 and 708, respectively) may be configured to be held by the system 50 or, more specifically, the holder subassembly 800 (shown in FIG. 9). For example, the bottom layer 704 may have drilled holes or indentations for the holder 806 and/or prism 804 (both shown in FIG. 9) to engage. Using manufacturing methods, such as those discussed above, the layers 704, 706, and 708 are configured to form one or more channels 712 that extend between and are in flow communication with a fluidic inlet/outlet (I/O) port 714 at one end 697 (FIG. 6) of the flow cell body 702 and another fluidic inlet/outlet (I/O) port 716 at the other end 699. Furthermore, the flow cell body 702 may include one or more pump cavities 724, each of which is interposed between one end 699 of the channel 712 and one of the fluidic I/O ports 716. The pump cavity 724 is shaped to hold one or more electroosmotic (EO) pumps 730, which will be described in further detail below.

Figure 8:
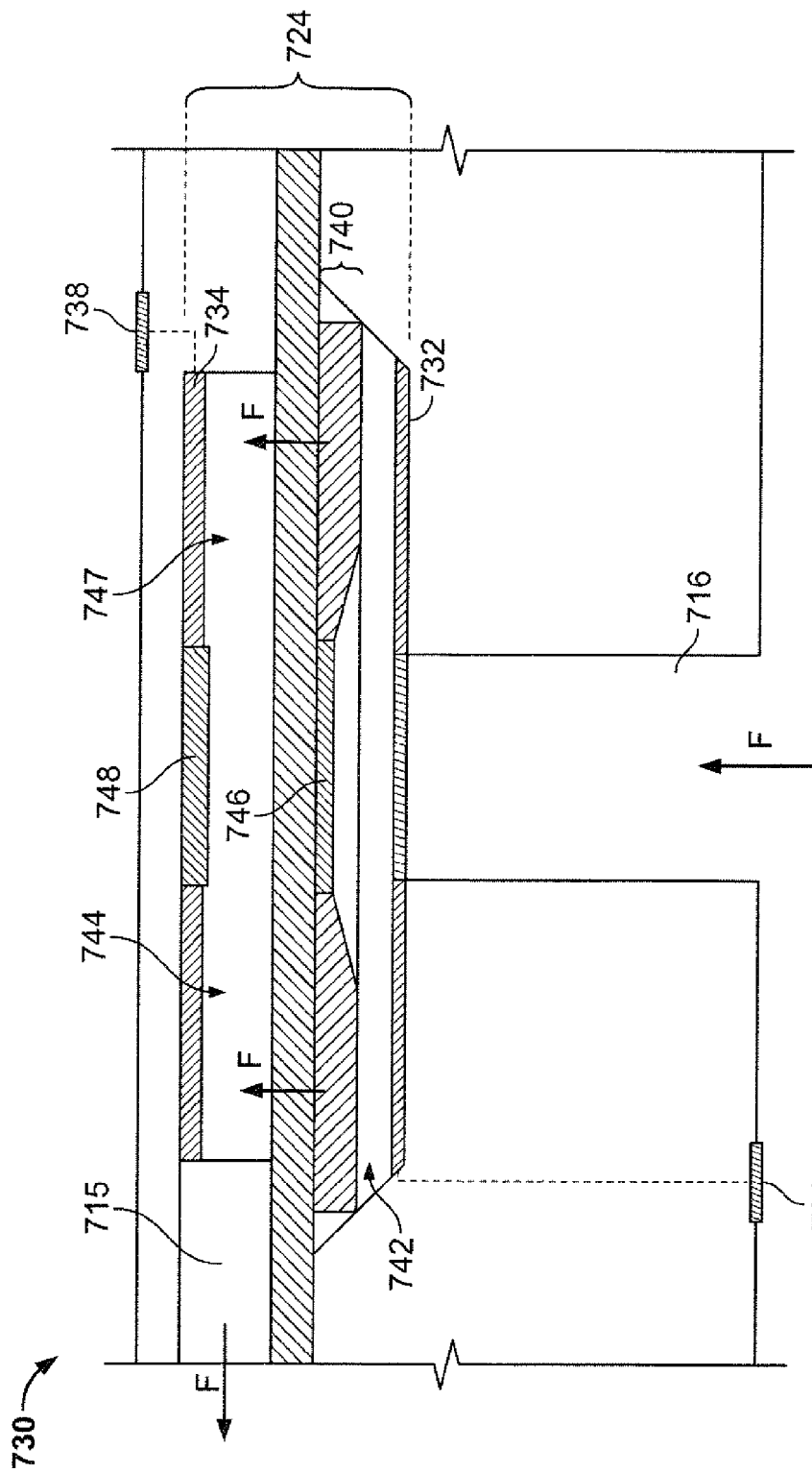
FIG. 8 is a cross-sectional view of a portion of the flow cell shown in FIG. 6.

FIG. 8 is an enlarged cross-sectional view of the flow cell 700 and, in particular, of the EO pump 730 within the pump cavity 724. In the embodiments shown, the pump cavity 724 is shaped to hold components of the EO pump 730 and direct fluid through one of the I/O ports (I/O port 716 in FIG. 8) and the connecting passage 715. The EO pump 730 includes at least two electrodes 732 and 734 that are positioned a predetermined distance apart and have bodies that extend in a direction substantially parallel with respect to each other. The electrodes 732 and 734 may be, for example, wire coil or disk-shaped electrodes. In addition, the electrode 732 may be connected to a contact 736 via an electrical path, and the electrode 734 may be connected to a contact 738. The electrodes 732 and 734 may be electrically charged by a power source (not shown). The power source may be a battery, AC power supply, DC power supply, or any other source. In FIG. 8, the electrode 732 is positively charged and operates as an anode. The electrode 734 is negatively charged and operates as a cathode. Although the electrodes 732 and 734 are positioned against walls of the pump cavity 724 in FIG. 8, the electrodes may be positioned separate from the walls and closer to each other. Furthermore, surfaces of the pump cavity 724 may be coated in an insulating material to prevent current leakage. The insulating material may be, for example, silicon dioxide, silicon nitride, or multiple layers of these materials.

In an alternative embodiment, the charge may be created by inductive coupling rather than a direct electrical connection. For example, the contacts 738 and 736 may be replaced with inductive contacts. The inductive contacts may be embedded below the upper and/or lower surfaces of the top and bottom layers of the flow cell. The inductive contacts may be covered in insulation to avoid direct exposure to surrounding environment. In operation, the flow cell holder would include transformer sources proximate the areas on the flow cell where the inductive contacts are to be positioned. Once the flow cell is placed in the holder, the transformer sources would create local electromagnetic fields in the areas surrounding the inductive contacts. The EM fields would induce current flow at the inductive contacts, thereby creating a voltage potential between the inductive contacts.

The EO pump 730 includes a porous membrane core 740 that is interposed between the electrodes 732 and 734. The core 740 includes a number of small pathways allowing the fluid to flow therethrough. The core 740 has a shape that extends across the pump cavity 724 such that the core 740 substantially separates the pump cavity 724 into two reservoirs 742 and 744. In FIG. 8, the core 740 is substantially tubular-shaped. However, in alternative embodiments, the core 740 may have disk, frustro-conical, concave, convex, or trapezoidal configurations or features, which may be designed to direct gases generated during the operation of the EO pump 730 to a gas collection area 747 (discussed in more detail below). The core 740 may be a porous structure having micron-sized pathways generally leading from one side of the porous structure to the other side. The core 740 may also be configured to have certain properties such as, high porosity and high electroosmotic mobility. For example, the core 740 may be a sintered glass (i.e., frit core) or a porous silicon membrane. In an alternative embodiment, the core 740 includes a series of slots that extend parallel to each other and are separated by trenches. Due to the electroosmotic effect, when an electric potential is applied between the electrodes 732 and 734, the fluid flows through the core 740 from the reservoir 742 to the reservoir 744. In addition to the properties of the core 740, the flow rate is dependent upon the properties of the fluid (i.e., molarity and pH) and the voltage potential maintained between the electrodes 732 and 734.

In some embodiments, the applied electrical potential at the electrodes 732 and 734 leads to electrolytic decomposition (i.e., gas is generated near the electrodes 732 and 734). For example, $H_2$ may be generated near the electrode 734 and $O_2$ may be generated near the electrode 732. Because the gases have a lower density than the fluid, the gas rises toward the top of the pump cavity 724. As shown in FIG. 8, the EO pump 730 may include a vapor permeable membrane 746. The membrane 746 is permeable to the gases generated near the electrode 732 (e.g., $O_2$) and may be fabricated from, for example, polytetrafluoroethylene (PTFE). The membrane 746 may be positioned in the center hole of the tubular-shaped core 740. The core 740, in turn, may be shaped to direct the gases generated to a collection area 747 near a catalyst member 748 within the reservoir 744. The catalyst member 748 operates to recombine the gases generated by the electrodes 732 and 734 and could be made from Platinum (Pt). When the gases mix in the reservoir 744, the catalyst member 748 facilitates recombining the $H_2$ and $O_2$ gases into water, which then rejoins the fluid within the reservoir 744.

Alternatively, the EO pump 730 may include a venting device (not shown) positioned near the gas collection area 747. The venting device may allow the gases generated by the electrodes 732 and 734 to be removed from the pump cavity 724 and released into the ambient air. For example, the top of the pump cavity 724 may have a frustro-conical shape that forms a pocket where the gases may collect. The venting device could be, for example, another vapor permeable membrane that is positioned between the ambient air and the pocket of air. When the gases collect in the pocket formed by the pump cavity 724, the pressure created by the fluid against the gases facilitates forcing the gases through the membrane.

The components of the EO pump 730 described above may be fastened or sealed together such that the components of the EO pump 730 form an integrated unit. For example, the components may be affixed within an acrylic housing. As such, the flow cell 700 may be configured to allow the EO pump 730 to be replaced by another EO pump unit when the EO pump 730 fails or another EO pump with different properties is desired.

Furthermore, the flow cell 700 is a "bottom flow" flow cell. Thus, as opposed to the flow cells, e.g., as shown in FIGS. 3-5 where the fluid may enter from the top side of the flow cell, some flow cells may have configurations that allow fluid flow that enters from the bottom of the flow cell. In some embodiments, bottom flow cells may have less fluidic dead volume (and use more of the whole channel length than top flow cells, e.g., since the ends of the flow cells are not covered by clamps/manifolds, etc.). Also, the bottom flow cells may be held to the flow cell holder through vacuum chucking rather than clamps. Thus, a vacuum can hold the flow cell into the correct position within the device so that proper illumination and imaging can take place.

In addition, the flow cell 700 illustrates a "push" flow cell in that the EO pump 730 is positioned upstream from the channel 712 (FIG. 7) and forces the fluid into the channels 712 via the connecting passage 715 where the reactions may occur. In alternative embodiments, the EO pump 730 is a "pull" flow cell in that the EO pump 730 is placed downstream from the channel 712 (i.e., after the reactions have occurred) such that the EO pump 730 draws the solution or fluid through the channel 712 before the fluid enters the pump. In such an embodiment, gases generated by the electrodes 732 and 734 are less likely to enter into the channels 712 and possibly disturb the readings of refracted light.

Figure 9:
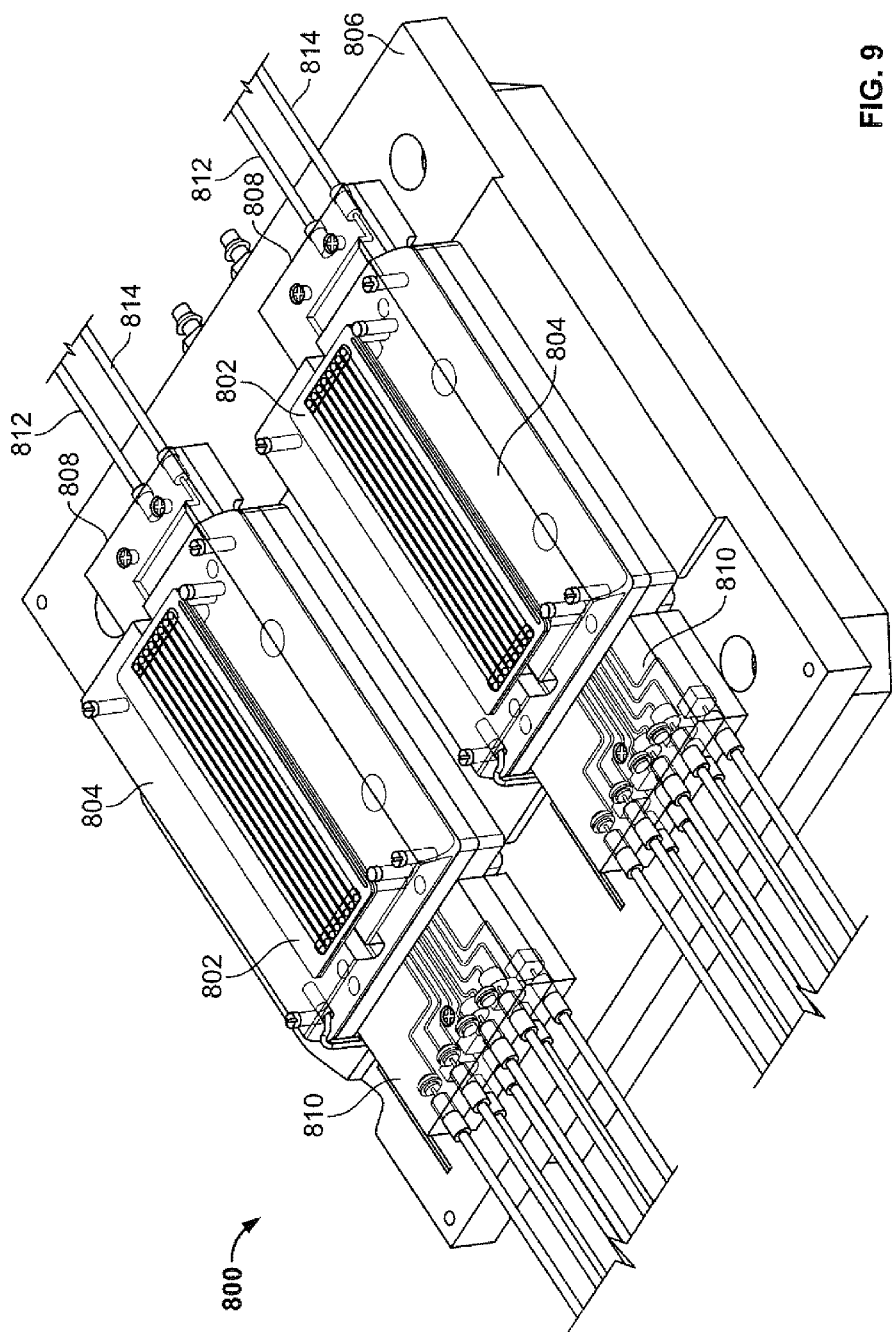
FIG. 9 is a perspective view of a holder subassembly formed in accordance with one embodiment.

FIG. 9 is a perspective view of a holder subassembly 800 that may be formed in accordance with one embodiment. The subassembly 800 is configured to hold flow cells 802 while the reader system (not shown) takes readings. The flow cells 802 may be similar to the flow cells discussed above. The subassembly 800 includes a holder 806 that is configured to support one or more inlet manifolds 808, prisms 804, flow cells 802, and outlet manifolds 810. As shown, each flow cell 802 is in flow communication with one inlet manifold 808 and one outlet manifold 810. A line 812 may provide the working fluid to the inlet manifold 808 in which an inner passageway (not shown) bifurcates and delivers the fluid to each of the channels on the flow cells 802. The holder 806 may have the prisms 804 fastened thereto by using, for example, screws. Each prism 804 is configured to hold one of the flow cells 802 and is configured to facilitate the reading process by refracting and/or reflecting the light that is generated by, for example, a laser. The subassembly 800 may also include a suction device/vacuum chuck positioned under each flow cell 802 that creates a vacuum (or partial vacuum) for holding the corresponding flow cell 802 and/or corresponding prism 804 to the holder 806. In one embodiment, the vacuum chuck may include a heating device or thermally conductive rim/member that contacts the flow cell and regulates the temperature of the flow cell in addition to holding the flow cell or prism in position. A line 814 may, for example, be connected to a vacuum for providing the negative pressure to hold the flow cells 802 against the corresponding prisms 804.

Figure 10:
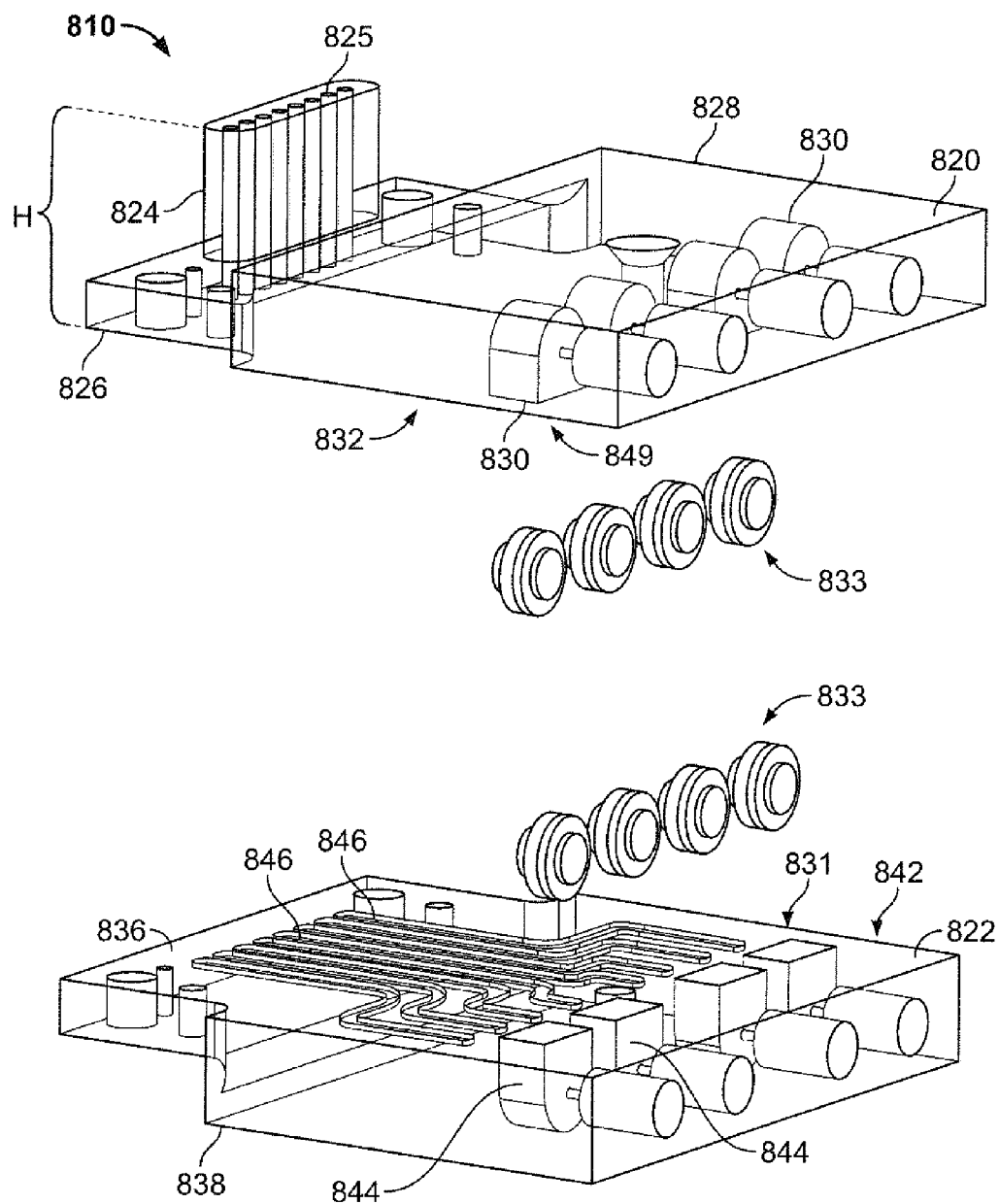
FIG. 10 is an exploded perspective view of an outlet manifold formed in accordance with one embodiment.

FIG. 10 is an exploded perspective view of the components used to form the outlet manifold 810. The manifold 810 includes a housing 811 (shown in FIG. 11) that may be formed from two layers 820 and 822. The layer 820 includes a channel connector 824 that extends from a base 826. The channel connector 824 includes one or more passages 825 that are configured to couple with the channels in the flow cell 802. The layer 820 also includes a lateral surface 832. The passages 825 extend a vertical distance H through the connector 824 and the base 826 to the lateral surface 832. The base 826 extends laterally outward from a body 828. The body 828 includes one or more pump cavities 830 that are in flow communication with passages 834 (shown in FIG. 11). The pump cavities 830 have access openings 849 for allowing EO pumps 833 to be inserted therein. Also shown in FIG. 10, the layer 822 includes a base 836 that extends laterally outward from a body 838. The base 836 and body 838 share a lateral surface 842 that has one or more channel grooves 846 formed therein. The channel grooves 846 form a flared pattern. Furthermore, the layer 822 includes a plurality of pump cavities 844 where each pump cavity 848 has an access opening 831 to allow one of the EO pumps 833 to be inserted. To form the manifold 810, the layers 820 and 822 are secured together. For example, an epoxy may be applied to the lateral surfaces 832 and 842 which may then be thermally bonded together.

Figure 11:
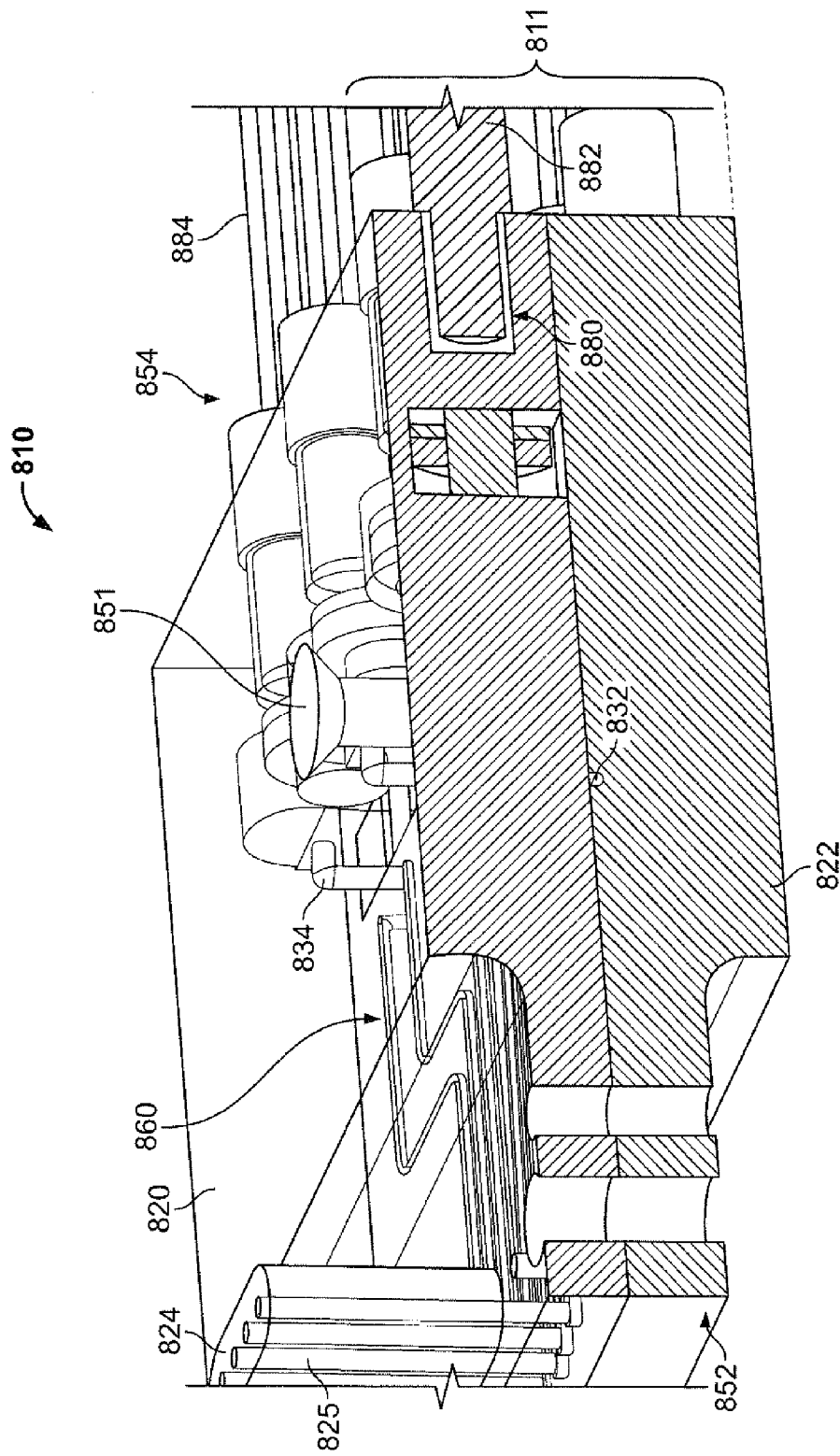
FIG. 11 is a cross-sectional view of the manifold in FIG. 10 in a constructed form.

FIG. 11 illustrates a cross-sectional view of the manifold 810 after the layers 820 and 822 have been secured together. When constructed, the manifold 810 has a detector engaging end 852 and a line terminating end 854. The corresponding connector passages 825, channel grooves 846, and passages 834 form one channel 860 that extends from the detector engaging end 852 to the line terminating end 854. The line terminating end 854 includes a receptacle 880 that is in flow communication between the pump cavity 830 (FIG. 10) and a discharge line 884. A sealing member 882 is secured to the receptacle 880 and couples the discharge line 884 to an I/O port 916 (FIG. 12) of the pump cavity 830. Furthermore, the manifold 810 may be fastened to the holder 806 (FIG. 9) using a screw hole 851. When the manifold 810 is in operation, the connector 824 is sealably connected to the flow cell 802 (FIG. 9) such that each channel 860 connects to a corresponding channel in the flow cell 802. By distributing the channels 860 in a flared pattern, the ED pumps 833 may be fitted with larger components (e.g., electrodes and porous core) thereby allowing a greater flow rate. Furthermore, by distributing the pump cavities 830 between the two layers 820 and 822 more EO pumps 833 may be used within the predetermined width of the manifold 810.

Figure 12:
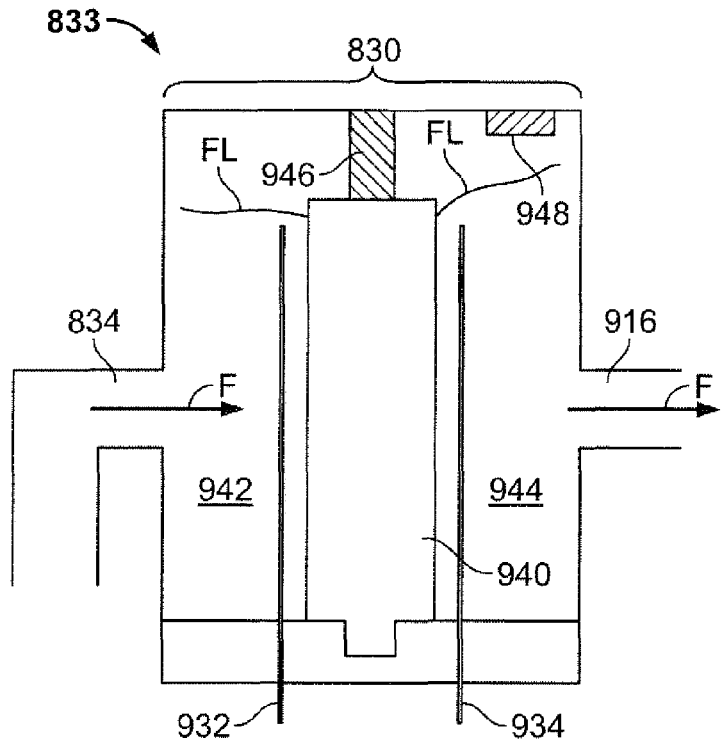
FIG. 12 is a cross-sectional view of an EO pump that may be used with the manifold in FIG. 11.

FIG. 12 is a cross-section of the EO pump 833. Although the EO pump 833 is discussed with reference to the manifold 810, the EO pump 833 may also be used in flow cells. As shown, the pump cavity 830 is in flow communication with the passage 834 and an I/O port 916 which leads to the discharge line 884 (FIG. 11). The EO pump 833 includes at least two electrodes 932 and 934 that are positioned a predetermined distance apart and have bodies that extend in a direction substantially parallel with respect to each other. The electrodes 932 and 934 may be, for example, wire coil electrodes so as to not substantially disrupt the flow of the fluid. The electrodes 932 and 934 may be electrically connected to contacts (not shown) which are, in turn, connected to a power source. In FIG. 12, the electrode 932 is positively charged and operates as an anode. And the electrode 934 is negatively charged and operates as a cathode.

The EO pump 833 also includes a core 940 that is interposed between the electrodes 932 and 934. The core 940 may be similar to the core 740 described above and includes a number of small pathways allowing the fluid to flow therethrough. The core 940 has a shape that extends across the pump cavity 930 such that the core 940 substantially separates the pump cavity 930 into two reservoirs 942 and 944. When an electric potential is applied between the electrodes 932 and 934, the fluid flows through the core 940 from the reservoir 942 to the reservoir 944. As described above, the applied electrical potentials may lead to the generation of gases (e.g., $H_2$ generated near the electrode 934 and $O_2$ generated near the electrode 932). The gas rises toward the top of the pump cavity 930 thereby avoiding the core 940 so that the gases do not interfere with the fluid flow through the core 940. As shown, the gases may form pockets at the top of the pump cavity 830 (illustrated by the fill lines FL).

As shown in FIG. 12, the EO pump 833 may include a vapor permeable membrane 946, which may be fabricated from, for example, polytetrafluoroethylene (PTFE). The membrane 946 may be positioned above the core 940 and, in one example, may form a collar that surrounds a portion of a perimeter of the core 940. The membrane 946 allows the $O_2$ gas to pass from the reservoir 942 to the reservoir 944. Also shown, the EO pump 833 may include a catalyst member 948 within the reservoir 944. Similar to the catalyst member 748, the catalyst member 948 operates as a catalyst for recombining the gases generated by the electrodes 932 and 934. The membrane 946 and catalyst member 748 may be located proximate to the core 940 in an area in which gases collect once generated during operation of the EO pump 833. When the gases mix in the reservoir 944, the catalyst member 948 facilitates recombining the $H_2$ and $O_2$ gases into water, which may then rejoin the fluid within the reservoir 944.

Figure 13:
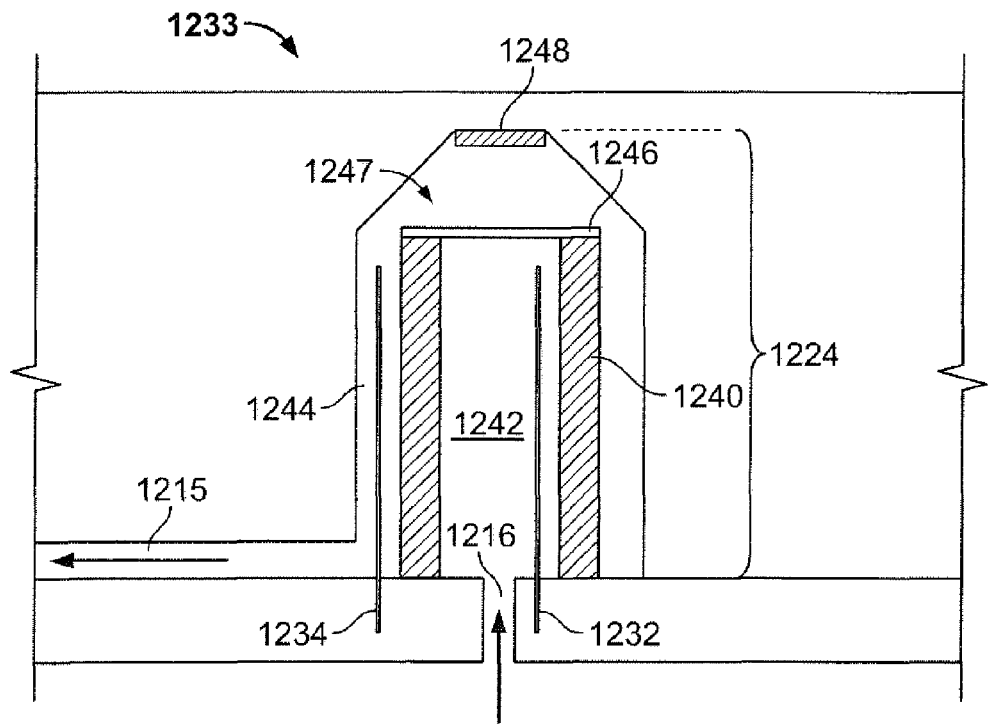
FIG. 13 is a cross-sectional view of an EO pump formed in accordance with an alternative embodiment

FIG. 13 is a cross-sectional view of an EO pump 1233 formed in accordance with an alternative embodiment. The BO pump 1233 may be used or integrated with the flow cells and/or the manifolds discussed herein. Furthermore, the EO pump 1233 may be positioned upstream or downstream from corresponding channels (not show) within a flow cell (not shown). Similar to the EO pumps 730 and 833, the EO pump 1233 is positioned within a pump cavity 1224. The EO pump 1233 includes at least two electrodes 1232 and 1234 that are positioned a predetermined distance apart and have bodies that extend in a direction substantially parallel with respect to each other. The electrodes 1232 and 1234 may be electrically connected to contacts (not shown), which are connected to a power source (not shown). In FIG. 13, the electrode 1232 is positively charged and operates as an anode, and the electrode 1234 is negatively charged and operates as a cathode. The EO pump 1233 also includes a core 1240 that is interposed between the electrodes 1232 and 1234. The core 1240 may be similar to the core 740 and 940 described above and includes a number of small pathways allowing the fluid to flow therethrough.

As shown in FIG. 13, the core 1240 has a shape that surrounds the electrode 1232. The core 1240 may have one portion that encircles the electrode 1232 or may include two portions that have the electrode 1232 interposed therebetween. When an electric potential is applied between the electrodes 1232 and 1234, the fluid flows through the core 1240 from an inner reservoir 1242 to an outer reservoir 1244. As described above, the applied electrical potentials may lead to the generation of gases (e.g., $H_2$ generated near the electrode 1234 and $O_2$ generated near the electrode 1232). The gas rises toward the top of the pump cavity 1224 thereby avoiding the core 1240 so that the gases do not interfere with the fluid flow through the core 1240. The EO pump 1233 may also include a vapor permeable membrane 1246, which may be fabricated from, for example, polytetrafluoroethylene (PTFE). The membrane 1246 may be positioned above the core 1240 and, in one example, may form a top that covers the core 1240. The membrane 1246 allows the $O_2$ gas to pass from the reservoir 1242 to the reservoir 1244. Also shown, the EO pump 1233 may include a catalyst member 1248 within the pump cavity 1224. Similar to the catalyst member 748 and 948, the catalyst member 1248 operates as a catalyst for recombining the gases generated by the electrodes 1232 and 1234. The membrane 1246 and catalyst member 1248 may be located proximate to the core 1240 and define a gas collection area 1247 therebetween where gases collect. When the gases mix in the collection area 1247, the catalyst member 1248 facilitates recombining the $H_2$ and $O_2$ gases into water, which may then rejoin the fluid within the reservoir 1244.

In FIG. 13, the membrane 1246 is positioned below the catalyst member 1248 such that when the gases recombine to form water, the water may fall upon the membrane 1246. In an alternative embodiment, the catalyst member 1247 is not positioned directly above the membrane 1246 such that the water would fall upon the membrane 1246. More specifically, the pump cavity 1224 may be configured to direct the gases to a gas collection area that is not directly above the membrane 1246. For example, the gas collection area 1247 and the catalyst member 1248 may be positioned above the electrode 1234 shown in FIG. 13. When the gases recombine, the water may fall directly into fluid held by the reservoir 1244 near the electrode 1234 thereby not falling upon the membrane 1246.

Figure 14:
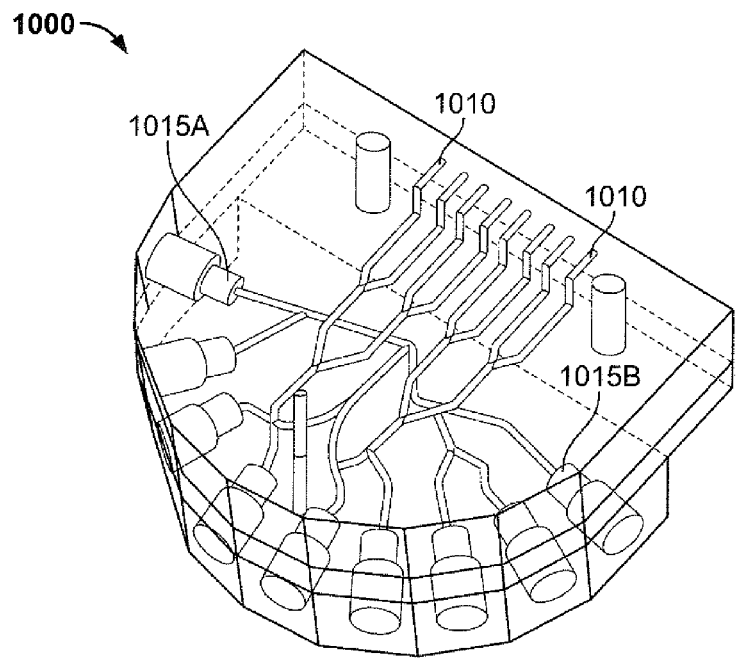
FIG. 14 is a perspective view of a manifold formed in accordance with an alternative embodiment.
Figure 15:
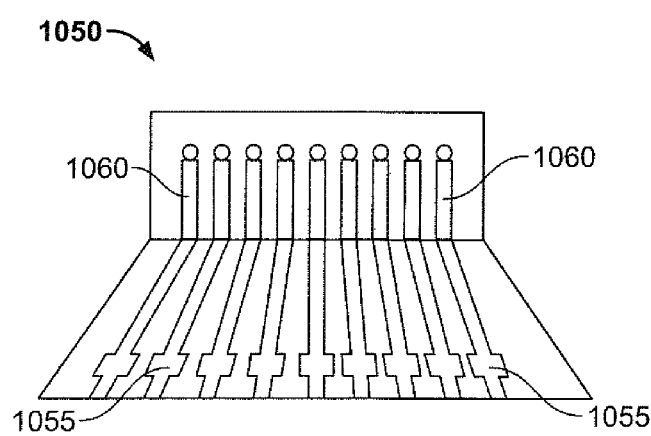
FIG. 15 is a planar view of a manifold formed in accordance with an alternative embodiment.

FIGS. 14 and 15 illustrate manifolds 1000 and 1050, respectively, that may be formed in accordance with alternative embodiments. FIG. 14 is a perspective view of the outlet manifold 1000. The outlet manifold 1000 has a number of branching channels 1010 that merge and diverge from each other. Each channel 1010 is in fluid communication with one or more EO pumps 1015, as each EO pump 1015 is in fluid communication with one or more channel 1010. The manifold 1000 sealably connects to a flow cell, such as those described above. The manifold 1000 allows an operator to use different EO pumps 1015 for different types of solution. For example, an operator may use the EO pump 1015A for a buffer solution and, separately, use the EO pump 1015B for a reagent solution. As such, the flow rate of the fluid in each flow cell channel (not shown) may be controlled by more than one EO pump 1015. Alternatively, the EO pumps 1015A and 1015B may be used simultaneously.

FIG. 15 is a planar view of an inlet manifold 1050 and illustrates a "push" manifold that includes several EO pumps 1055 that are positioned upstream from a flow cell, such as those discussed above. The manifold 1050 forces the fluid through channels 1060, which sealably engage with channels from the flow cell where reactions may occur.

Furthermore, multiple EO pumps may be used either in series (i.e., cascade) or in a parallel with respect to one channel. Furthermore, the EO pumps 730, 833, 1015, and 1055 described above are bi-directional in that the direction of flow may be reversed by changing the polarity of the corresponding electrodes and (if necessary) repositioning the catalyst member or membrane. In one embodiment, the EO pump is integrated and held together by a housing thereby allowing a user to flip the EO pump causing the flow to change direction.

Figure 16:
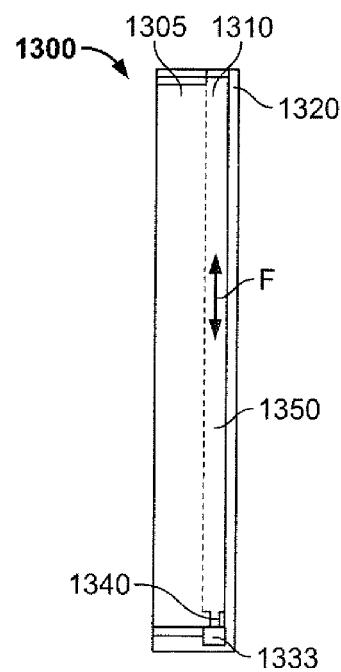
FIG. 16 is a flow cell formed in accordance with an alternative embodiment

FIG. 16 is a flow cell 1300 formed in accordance with an alternative embodiment. The flow cell 1300 may be similarly fabricated as discussed above and may include a base layer 1305, a channel layer 1310, and a cover layer 1320. The flow cell 1300 is configured to be held vertically (i.e., the fluid flow within channels 1350 is substantially aligned with the force of gravity) by the system 50 while the flow cell 1300 is being read. The fluid flow could either be toward an EO pump 1333 or away from the EO pump 1333. The EO pumps 1333 that may be similarly configured to the EO pumps discussed above. However, the EO pumps 1333 may be, for example, rotated about 90 degrees with respect to the orientation shown above so that the gases generated by the electrodes (not shown) may rise to the designated gas collection area. The flow cell 1300 also includes passages 1340 in flow communication with the channels 1350 and EO pumps 1333. In one embodiment, the EO pump 1333 functions and operates similarly to the EO pumps discussed above. Alternatively, as will be discussed below, the EO pump 1333 may operate and function similar to a valve in controlling the direction and flow rate of the fluid through channels 1350.

FIG. 17 is a planar view of a flow cell 1400 formed in accordance with an alternative embodiment. FIG. 17 illustrates channels having inlets and outlets on the same end of the flow cell 1400. More specifically, the flow cell 1400 includes a plurality of channels 1410, 1420, 1430, and 1440. Although the following is directed toward the flow cell 1400, the description of the channels 1410, 1420, 1430, and 1440 may similarly be applied to the other flow cells described herein. The channel 1410 has an inlet hole 1411 at an end 1450 and extends a length of the flow cell 1400 to another end 1460. The channel 1410 then turns and extends back toward the end 1450 until the channel 1410 reaches an outlet hole 1412. The channel 1420 includes an inlet hole 1421 and extends down toward the end 1460. When proximate to the end 1460, the channel 1420 then turns and extends back toward the end 1450 and outlet 1422. As shown in FIG. 17, the channel 1420 abruptly or sharply turns back toward the end 1450 such that the portion of channel 1420 extending from end 1450 to end 1460 is adjacent to or shares a wall with the portion of channel 1420 extending from end 1460 to end 1450. At the end 1460, the channel 1420 may turn within the channel layer or may turn into other layers (not shown) including extending out of the flow cell 1400 before returning to the channel layer.

Also shown in FIG. 17, the channels 1430 and 1440 extend parallel and adjacent to each other within the flow cell 1400. The channel 1430 includes an inlet hole 1431 and an outlet hole 1432. The channel 1440 includes an inlet hole 1441 and an outlet hole 1442. As shown, the flow of fluid $F_5$ is opposite in direction to the flow of fluid $F_6$. In some embodiments, the fluid within the channels 1430 and 1440 belong to separate lines of a fluid flow system. Alternatively, the fluid within the channels 1430 and 1440 belong to a common line of the fluid flow system such that the fluid flowing through the outlet 1432 either immediately or eventually returns to the channel 1440 through inlet 1441.

FIG. 18 is a planar view of a flow cell 1500 that integrates one or more heating mechanisms. The flow cell 1500 illustrates a plurality of channels 1510, 1520, 1530, 1540, 1550, 1560, and 1570 all of which include inlet EO pumps 1580 that are upstream from the corresponding channel. Alternatively, the EO pumps may be outlets that are positioned downstream from the corresponding channel. The channel 1510 is in flow communication with the corresponding EO pump 1580 and includes a passage that runs adjacent or proximate to a contact pad 1590. The pad 1590 is configured to generate thermal energy (or, alternatively, absorb thermal energy) for regulating the temperature of the fluid within the channel 1510. The pad 1590 may be made from a metal alloy and/or another thermally conductive material. Also shown, the channels 1520 and 1530 extend adjacent to each other and include a trace 1595 that extends between the channels 1520 and 1530. Similar to the pad 1590, the trace 1595 is configured to regulate the temperature of the fluid within the channels 1520 and 1530 and may be made from a metal alloy and/or another thermally conductive material. Alternatively, each trace 1595 (if more than one) may only be used with one corresponding channel. Furthermore, the channel 1540 utilizes a trace 1596 that extends the bottom of the channel 1540 and functions similarly to the trace 1595.

Also shown in FIG. 18, the flow cell 1500 may utilize an additional channel 1560 to regulate the temperature of adjacent channels 1550 and 1570. More specifically, fluid flowing through the channel 1560 may have a predetermined temperature (determined by the computing system or operator) that generates thermal energy for or absorbs thermal energy from the adjacent channels 1550 and 1570. Although flow cell 1500 illustrates several types of integrated heating mechanisms, the flow cell 1500 (or other flow cells described herein) may use only one or more than one within the same flow cell if desired. Furthermore, more than one heating mechanism may be used for each channel. For example, one side of the channel may be kept warmer by a trace that generates heat. The other side of the channel may be cooler by a trace that absorbs thermal energy.

Figure 19:
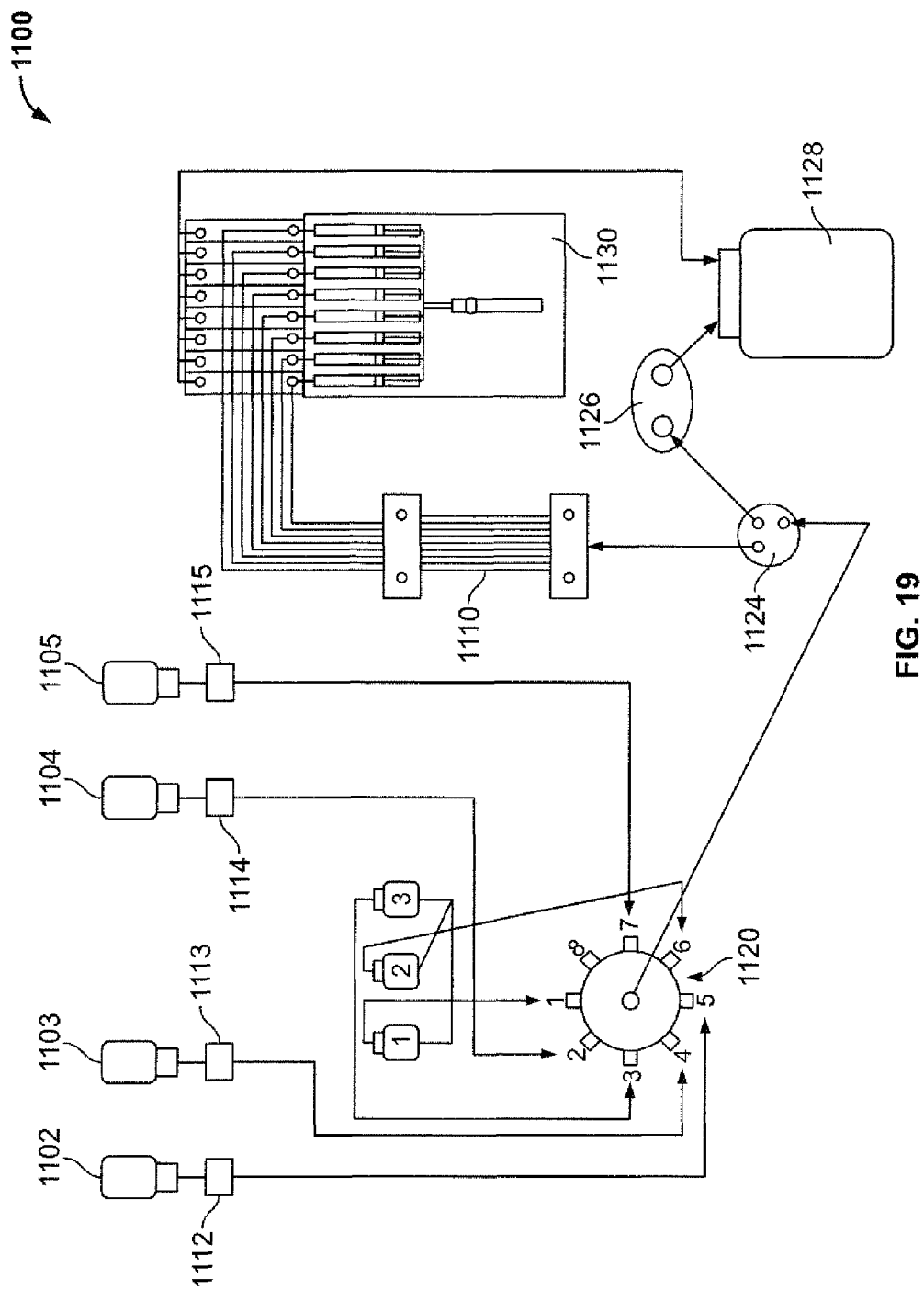
FIG. 19 is a diagram of a fluid flow system formed in accordance with one embodiment.

FIG. 19 illustrates a fluid flow system 1100 formed in accordance with one embodiment. The fluid flow system 1100 may be used with any system, such as system 50, that utilizes fluidics or microfluidics in delivering different types of solutions to different devices or systems. In addition, the fluid flow system 1100 may use any of the flow cells and manifolds discussed herein. As shown, the fluid flow system 1100 includes a plurality of solution containers 1102-1105 that hold corresponding reagents or solutions. Each container 1102-1105 is in fluid communication with a corresponding electroosmotic (EO) switch 1112-1115. The EO switches 1112-1115 include parts and components similar to those discussed above with reference to EO pumps 730 and 833. However, the EO switches 1112-1115 function and operate similar to valves. More specifically, the EO switches 1112-1115 resist fluidic motion in one direction. When the operator or computing system desires that a solution from one of the containers 1102-1105 be used, the voltage differential is reduced or turned off altogether.

As shown in FIG. 16, the fluid flow system 1100 may include a multi-valve 1120, which may or may not utilize EO switches, such as EO switches 1112-1115. The multi-valve 1120 may mix the solutions from the containers 1102-1105 with each other or with other solutions (e.g., with water for diluting). The solutions may then be directed toward a priming valve (or waste valve 1124), which may be connected to an optional priming pump 1126. The priming pump 1126 may be used to draw the solutions from the corresponding containers 1112-1115. The priming valve 1124 (which may or may not include an EO switch) may then direct the solutions into a detector system, such as system 50, or into a flow cell 1110. Alternatively, solutions are directed into a manifold (not shown) attached to the flow cell 1110. The flow cell 1110 may or may not contain an EO pump, such as those discussed above. The fluid flow system 1100 may also include a channel pump 1130, which may draw the solutions through the corresponding channels and optionally direct the solutions into a waste reservoir.

As discussed above, the many switches, valves, and pumps of the fluid flow system 1100 may be controlled by a controller or computing system which may be automated or controlled by an operator.

Furthermore, the positioning, size, path, and cross-sectional shape of the channels in the flow cells and the manifold housing may all be configured for a desired flow rate and/or design for using with the detector system 50. For example, the pump cavities 830 in FIG. 10 may have a co-planar relationship with respect to each other.

It is to be understood that the above description is intended to be illustrative, and not restrictive. As such, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments.

Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." The term "comprising" is intended herein to be open-ended, including not only the recited elements, but further encompassing any additional elements. Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A flow cell for use in a microfluidic detection system, comprising:
    a flow cell body having a channel extending along the flow cell body, the flow cell body comprising a substrate material that extends along the channel and that is transparent to at least one of excitation light or light emissions, the channel having a functionalized channel surface that includes reactive groups immobilized thereto that are configured to attach to molecules for biochemical analysis;
    fluidic inlet and fluidic outlet ports provided on the flow cell body, the inlet and outlet ports being in fluid communication through the channel; and
    an electroosmotic (EO) pump held within the flow cell body in fluid communication with the channel, the EO pump being operable to induce flow of a solution from the inlet port to the outlet port and along the functionalized channel surface, wherein the EO pump includes a porous membrane core and a vapor permeable membrane that separate the fluidic inlet and outlet ports, the EO pump inducing flow of the solution through the porous membrane core and through the channel between the fluidic inlet and outlet ports, the vapor permeable membrane permitting gases generated during operation of the EO pump to pass through the vapor permeable membrane and bypass the porous membrane core; and
    wherein a pump cavity provided in the flow cell body comprises first and second reservoirs that are separated by the vapor permeable membrane and the porous membrane core, the vapor permeable membrane being positioned with respect to the first reservoir and a gravitational force direction so that the gases generated in the first reservoir during operation of the EO pump float toward the vapor permeable membrane, the gases passing through the vapor permeable membrane into the second reservoir thereby bypassing the porous membrane core;
    wherein the porous membrane core has a core edge that defines a hole of the porous membrane core, the vapor permeable membrane being positioned within the hole, the EO pump configured to be oriented with respect to the gravitational force direction such that the gases generated in the first reservoir float to the vapor permeable membrane and thereby bypass the porous membrane core through the hole.

2. The flow cell of claim 1, wherein the flow cell body includes an exterior surface, the flow cell body being sized and shaped to permit a detection system to scan along the exterior surface to image light emissions from the functionalized channel surface within the channel.

3. The flow cell of claim 1, wherein the flow cell body includes an exterior surface that extends substantially parallel to the channel surface for a majority of the length of the functionalized channel surface.

4. The flow cell of claim 1, wherein the flow cell body includes an exterior surface and wherein a substantially uniform thickness of the substrate material exists between the channel and the exterior surface.

5. The flow cell of claim 1, wherein the flow cell body consists essentially of attached substrate layers and conductive pathways to the EO pump.

6. The flow cell of claim 5, wherein the flow cell body includes a plurality of the channels and a plurality of the EO pumps.

7. The flow cell of claim 1, wherein the flow cell body is an elongated structure that extends lengthwise between two ends and has a detection region therebetween, the detection region comprising a majority of a length of the flow cell body.

8. The flow cell of claim 1, wherein the flow cell body includes a plurality of the channels that are coplanar with respect to each other through a detection region of the flow cell body.

9. The flow cell of claim 1, wherein the reactive groups include oligonucleotides immobilized thereto for nucleic acid cluster generation.

10. The flow cell of claim 1, further comprising a catalyst member that recombines the gases or a venting device that allows the gases to pass therethrough into an ambient environment.

11. The flow cell of claim 1, wherein the flow cell body includes a plurality of the inlet ports.

12. The flow cell of claim 11, wherein the flow cell body includes a plurality of the outlet ports, each of the outlet ports being in fluid communication with a single one of the inlet ports.

13. The flow cell of claim 1, wherein the porous membrane core is shaped to include a recess that is adjacent to the vapor permeable membrane in the first reservoir, the gases collecting in the recess and passing through the vapor permeable membrane into the second reservoir.

14. The flow cell of claim 1, wherein the flow cell is a unitary structure that is configured to be mounted onto a stage and removed therefrom as a unit, the fluidic inlet and outlet ports configured to couple to a fluid flow subsystem when mounted onto the stage such that the solution from the fluid flow subsystem flows through the channel when induced by the EO pump.

15. The flow cell of claim 14, wherein the EO pump comprises anode and cathode electrodes that are spaced apart having a porous membrane core therebetween, the anode and cathode electrodes inducing a flow rate of the solution through the porous membrane core based on a voltage potential maintained between the anode and cathode electrodes, wherein the EO pump is located at a downstream end of the channel, and wherein the anode electrode, the cathode electrode, and the porous membrane core are positioned relative to one another such that the EO pump draws the liquid through the fluidic inlet port and the channel before the liquid enters the EO pump.

16. The flow cell of claim 14, wherein the reactive groups include oligonucleotide primers that are immobilized to the functionalized channel surface before the flow cell is mounted onto the stage.

17. A system comprising the flow cell of claim 1, wherein the EO pump is located downstream from the functionalized surface in the channel, the system also comprising a fluid flow subsystem that is configured to be in flow communication with the channel of the flow cell, the fluid flow subsystem including a waste reservoir, wherein the EO pump of the flow cell directs the liquid to the waste reservoir after the EO pump draws the liquid along the functionalized channel surface.

18. A flow cell for use in a microfluidic detection system, comprising:
a flow cell body having a channel extending along the flow cell body, the flow cell body comprising a substrate material that extends along the channel and that is transparent to at least one of excitation light or light emissions, the channel having a functionalized channel surface that includes reactive groups immobilized thereto that are configured to attach to molecules for biochemical analysis;
fluidic inlet and fluidic outlet ports provided on the flow cell body, the inlet and outlet ports being in fluid communication through the channel; and
an electroosmotic (EO) pump held within the flow cell body in fluid communication with the channel, the EO pump being operable to induce flow of a solution from the inlet port to the outlet port and along the functionalized channel surface, wherein the EO pump includes a porous membrane core and a vapor permeable membrane that separate the fluidic inlet and outlet ports, the EO pump inducing flow of the solution through the porous membrane core and through the channel between the fluidic inlet and outlet ports, the vapor permeable membrane permitting gases generated during operation of the EO pump to pass through the vapor permeable membrane and bypass the porous membrane core; and
wherein a pump cavity provided in the flow cell body comprises first and second reservoirs that are separated by the vapor permeable membrane and the porous membrane core, the vapor permeable membrane being positioned with respect to the first reservoir and a gravitational force direction so that the gases generated in the first reservoir during operation of the EO pump float toward the vapor permeable membrane, the gases passing through the vapor permeable membrane into the second reservoir thereby bypassing the porous membrane core;
wherein the EO pump comprises anode and cathode electrodes that are spaced apart having a porous membrane core therebetween, the anode and cathode electrodes inducing a flow rate of the solution through the porous membrane core based on a voltage potential maintained between the anode and cathode electrodes;
wherein the EO pump is located downstream from the functionalized surface in the channel, and wherein the anode electrode, the cathode electrode, and the porous membrane core are positioned relative to one another such that the EO pump draws the liquid through the fluidic inlet port and the channel and along the functionalized channel surface before the liquid enters the EO pump.

19. A system comprising the flow cell of claim 18, the system also comprising a fluid flow subsystem that is configured to be in flow communication with the channel of the flow cell, the fluid flow subsystem including a waste reservoir, wherein the EO pump of the flow cell directs the liquid to the waste reservoir after the EO pump thaws the liquid along the functionalized channel surface.

20. The flow cell of claim 18, wherein the flow cell body includes an exterior surface that extends substantially parallel to the channel surface for a majority of the length of the functionalized channel surface, wherein a substantially uniform thickness of the substrate material exists between the channel and the exterior surface.

21. The flow cell of claim 18, wherein the flow cell body consists essentially of attached substrate layers and conductive pathways to the EO pump.

22. The flow cell of claim 18, wherein the flow cell body includes a plurality of the channels that are coplanar with respect to each other through a detection region of the flow cell body, wherein the flow cell body includes a plurality of the inlet ports and a plurality of the outlet ports, each of the outlet ports being in fluid communication with a single one of the inlet ports through a respective channel of the plurality of channels.

23. The flow cell of claim 18, wherein the reactive groups include oligonucleotides immobilized thereto for nucleic acid cluster generation.

24. The flow cell of claim 18, wherein the porous membrane core is shaped to include a recess that is adjacent to the vapor permeable membrane in the first reservoir, the gases collecting in the recess and passing through the vapor permeable membrane into the second reservoir.

25. A flow cell for use in a microfluidic detection system, comprising:
a flow cell body having a channel extending along the flow cell body, the flow cell body comprising a substrate material that extends along the channel and that is transparent to at least one of excitation light or light emissions, the channel having a functionalized channel surface that includes reactive groups configured to attach to molecules for biochemical analysis;
fluidic inlet and fluidic outlet ports provided on the flow cell body, the inlet and outlet ports being in fluid communication through the channel; and
an electroosmotic (EO) pump held within the flow cell body in fluid communication with the channel, the EO pump being operable to induce flow of a solution from the inlet port to the outlet port and along the functionalized channel surface, wherein the EO pump includes a porous membrane core and a vapor permeable membrane that separate the fluidic inlet and outlet ports, the EO pump inducing flow of the solution through the porous membrane core and through the channel between the fluidic inlet and outlet ports, the vapor permeable membrane permitting gases generated during operation of the EO pump to pass through the vapor permeable membrane and bypass the porous membrane core; and wherein a pump cavity provided in the flow cell body comprises first and second reservoirs that are separated by the vapor permeable membrane and the porous membrane core, the vapor permeable membrane being positioned with respect to the first reservoir and a gravitational force direction so that the gases generated in the first reservoir during operation of the EO pump float toward the vapor permeable membrane, the gases passing through the vapor permeable membrane into the second reservoir thereby bypassing the porous membrane core;

wherein the EO pump comprises anode and cathode electrodes that are spaced apart having a porous membrane core therebetween, the anode and cathode electrodes inducing a flow rate of the solution through the porous membrane core based on a voltage potential maintained between the anode and cathode electrodes; and wherein the porous membrane core and the electrodes are part of an integrated unit that is discrete with respect to the flow cell body and is configured to be positioned in the pump cavity as a unitary structure.

26. A system comprising the flow cell of claim 25, wherein the EO pump is located downstream from the functionalized surface in the channel, and wherein the anode electrode, the cathode electrode, and the porous membrane core are positioned relative to one another such that the EO pump draws the liquid through the fluidic inlet port and the channel and along the functionalized channel surface before the liquid enters the EO pump, the system also comprising a fluid flow subsystem that is configured to be in flow communication with the channel of the flow cell, the fluid flow subsystem including a waste reservoir, wherein the EO pump of the flow cell directs the liquid to the waste reservoir after the EO pump draws the liquid along the functionalized channel surface.

27. The flow cell of claim 25, wherein the flow cell body includes an exterior surface that extends substantially parallel to the channel surface for a majority of the length of the functionalized channel surface, wherein a substantially uniform thickness of the substrate material exists between the channel and the exterior surface.

28. The flow cell of claim 25, wherein the flow cell body consists essentially of attached substrate layers and conductive pathways to the EO pump.

29. The flow cell of claim 25, wherein the reactive groups include oligonucleotides immobilized thereto for nucleic acid cluster generation.

30. The flow cell of claim 25, wherein the flow cell body includes a plurality of the channels that are coplanar with respect to each other through a detection region of the flow cell body, wherein the flow cell body includes a plurality of the inlet ports and a plurality of the outlet ports, each of the outlet ports being in fluid communication with a single one of the inlet ports through a respective channel of the plurality of channels.

* * * * *